United States Patent
Hamada et al.

(10) Patent No.: US 10,395,364 B2
(45) Date of Patent: Aug. 27, 2019

(54) NUCLEAR MEDICAL IMAGE ANALYSIS TECHNIQUE

(71) Applicant: Nihon Medi-Physics Co., Ltd., Tokyo (JP)

(72) Inventors: Kazuo Hamada, Tokyo (JP); Hiromitsu Daisaki, Tokyo (JP); Kazumasa Nishida, Tokyo (JP)

(73) Assignee: Nihon Medi-Physics Co., Ltd., Tokyo (JP)

(*) Notice: Subject to any disclaimer, the term of this patent is extended or adjusted under 35 U.S.C. 154(b) by 120 days.

(21) Appl. No.: 15/509,244

(22) PCT Filed: Oct. 29, 2015

(86) PCT No.: PCT/JP2015/080508
§ 371 (c)(1),
(2) Date: Mar. 7, 2017

(87) PCT Pub. No.: WO2016/125349
PCT Pub. Date: Aug. 11, 2016

(65) Prior Publication Data
US 2018/0232877 A1    Aug. 16, 2018

(30) Foreign Application Priority Data

Feb. 4, 2015 (JP) .................. 2015-019831
Feb. 4, 2015 (JP) .................. 2015-019832
Feb. 4, 2015 (JP) .................. 2015-019833

(51) Int. Cl.
*G06K 9/00* (2006.01)
*G06T 7/00* (2017.01)
(Continued)

(52) U.S. Cl.
CPC ............ *G06T 7/0012* (2013.01); *G01T 1/161* (2013.01); *G06T 7/12* (2017.01); *G06T 7/13* (2017.01);
(Continued)

(58) Field of Classification Search
None
See application file for complete search history.

(56) References Cited

U.S. PATENT DOCUMENTS

2008/0008369 A1* 1/2008 Koptenko ............ G06K 9/4604
382/128
2008/0317314 A1* 12/2008 Schwartz .................. G06K 9/34
382/131

(Continued)

FOREIGN PATENT DOCUMENTS

JP    2007-14706    1/2007
JP    2010-4940     1/2010
(Continued)

OTHER PUBLICATIONS

Zhou, Xiangrong, et al., "Anatomical Structure Recognition of Normal Torso Region in Non-contrast CT Images", May 2006, Medical Imaging Technology, vol. 24, No. 3, (abstract only in English), 6 pgs.

*Primary Examiner* — Wei Wen Yang
(74) *Attorney, Agent, or Firm* — Harrington & Smith

(57) ABSTRACT

One embodiment of the present invention addresses the problem of reducing the influence of physiological accumulation in monitoring nuclear medical image data. To solve this problem, the embodiment includes: extracting a bone area from CT image data having been positioned with nuclear medical image data; in the nuclear medical image data, displaying the data of an area overlapping the bone area extracted above; and, in the nuclear medical image data,
(Continued)

not displaying the data of an area not overlapping the bone area extracted above.

17 Claims, 22 Drawing Sheets

(51) Int. Cl.
 *G01T 1/161*  (2006.01)
 *G06T 7/44*  (2017.01)
 *G06T 7/12*  (2017.01)
 *G06T 7/13*  (2017.01)
 *G16H 30/40*  (2018.01)

(52) U.S. Cl.
 CPC ............... *G06T 7/44* (2017.01); *G16H 30/40* (2018.01); *G06T 2207/10081* (2013.01); *G06T 2207/10104* (2013.01); *G06T 2207/10108* (2013.01); *G06T 2207/20101* (2013.01); *G06T 2207/20156* (2013.01); *G06T 2207/20168* (2013.01); *G06T 2207/30008* (2013.01); *G06T 2207/30096* (2013.01)

(56) References Cited

U.S. PATENT DOCUMENTS

| | | |
|---|---|---|
| 2011/0182489 A1 | 7/2011 | Chang et al. |
| 2013/0101197 A1* | 4/2013 | Kaftan ..................... G06T 5/00 382/131 |
| 2014/0148679 A1 | 5/2014 | Eary et al. |
| 2016/0203599 A1* | 7/2016 | Gillies .................. A61B 6/463 382/132 |

FOREIGN PATENT DOCUMENTS

| | | |
|---|---|---|
| JP | 2010-29481 | 2/2010 |
| JP | 2013-88386 | 5/2013 |
| JP | 2014-174654 | 9/2014 |

* cited by examiner

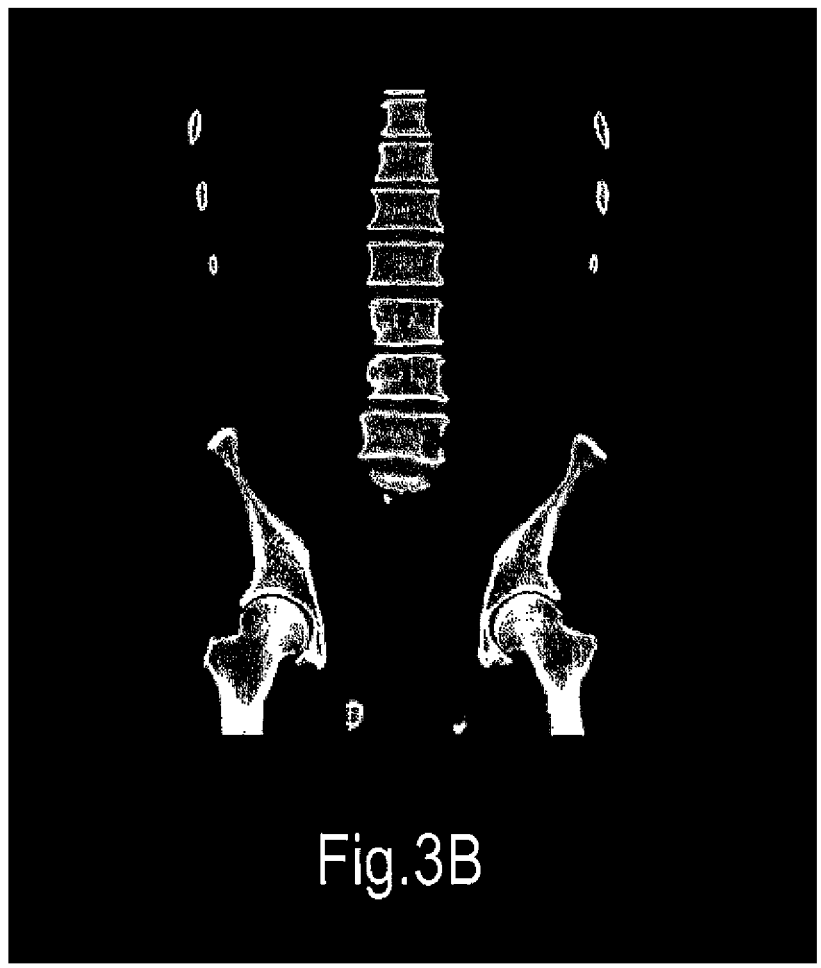

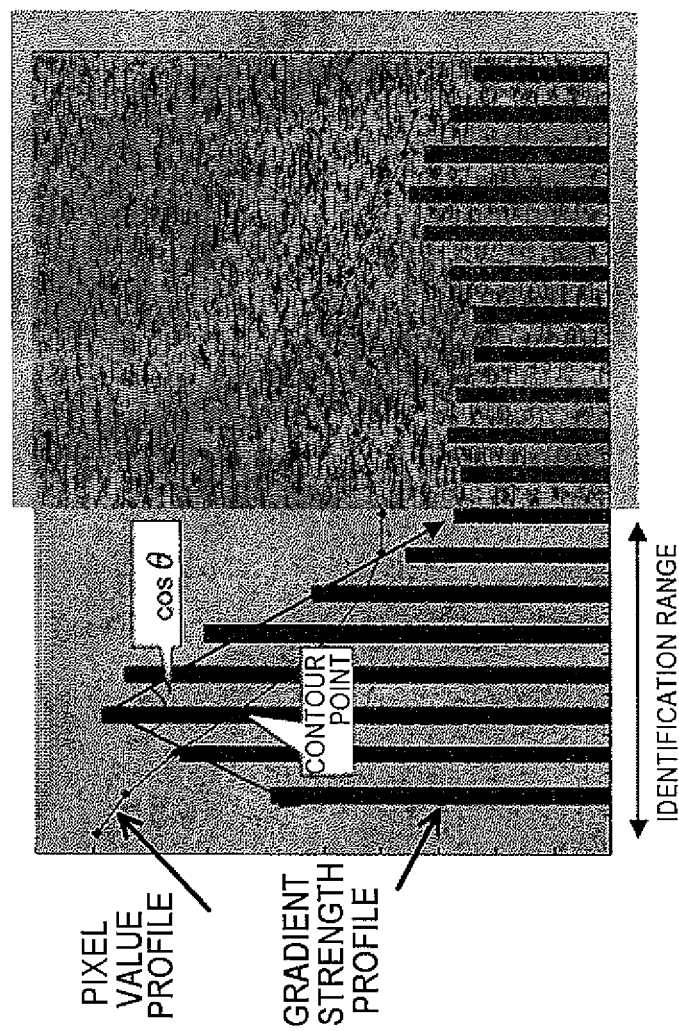

NUCLEAR MEDICAL IMAGE ANALYSIS TECHNIQUE

FIELD

The invention disclosed in the present application relates generally to a technique for analyzing nuclear medicine images. In some embodiments, the present invention specifically relates to a technique for extracting a tumor region in a nuclear medicine image. In some embodiments, the present invention specifically relates to a technique for extracting a tumor contour in a nuclear medicine image.

BACKGROUND

A single-photon emission computed tomography (SPECT) agent $^{99m}$Tc-HMDP and a positron emission tomography (PET) agent $^{18}$F—NaF are considered to be chemically absorbed mainly in hydroxyapatite crystals, which is the basic composition of bone minerals. Thus, a larger amount of such agents is absorbed in osteoblastic parts with increased bone turnover, allowing visualization of bone metastases of malignant tumors or inflammatory sites such as fractures, as areas of high accumulation of the agents.

The SPECT agent $^{99m}$Tc-HMDP is promptly distributed to bone tissues in the whole body after it is administered intravenously, and yields high-quality bone scintigrams one to two hours after the administration.

The PET agent $^{18}$F—NaF has reportedly yielded stable bone scintigrams in 30 minutes after the administration. PET allows precise correction of an decrease or scatter of agents within the body, which enables provision of highly quantitative images.

SUMMARY

Bone scintigrams allow qualitative (visual) detection of pathological lesions; however, it may cause accumulation in the kidneys and the bladder, which are excretion routes, thus hindering analysis.

In view of solving such a problem, the inventors of the present application disclose the invention including the following aspect relating to a technique for analyzing nuclear medicine image data. This aspect of the invention is characterized in that it includes:

extracting a bone region from computed tomography (CT) image data that has been aligned with the nuclear medicine image data;

displaying, from among the nuclear medicine image data, data of a region overlapping the extracted bone region; and not displaying, from among the nuclear medicine image data, data of a region not overlapping the extracted bone region.

For example, when analysis of bone scintigrams employs a conventional method of extracting, as a lesion, a region having values equal to or larger than a certain threshold, the kidneys and the bladder, which are subject to physiological accumulation, are also displayed and extracted as high accumulation sites. In contrast, the above aspect of the invention does not display data of a region not overlapping a bone region from among nuclear medicine image data. This configuration enables observation and analysis of nuclear medicine image data with the effect of accumulation due to normal physiological reasons excluded.

In the description and the claims of the present application, the term "nuclear medicine image data" indicates a concept including two-dimensional nuclear medicine image data and three-dimensional nuclear medicine image data. The above aspect of the invention is applicable to both two-dimensional nuclear medicine image data and three-dimensional nuclear medicine image data.

For observing a tumor with bone scintigrams, a region corresponding to the tumor may need to be extracted from nuclear medicine image data. Conventional techniques for this extraction include a method of displaying nuclear medicine image data on a display and tracing the contour of a tumor with a mouse or other means to extract the tumor, and a method of setting an appropriate pixel threshold and determining a region having pixel values equal to or larger than the threshold to be a tumor.

In the case of the former method, however, the size of the extracted tumor varies depending on the skill or preference of an operator. In the case of the latter method, the optimum threshold may need to vary depending on the conditions of a patient such as the dose of an agent and presence of physiological accumulation, the conditions of imaging, and the imaging apparatus. Consequently, tumors extracted by these two methods may vary in size.

In view of solving such a problem, the inventors of the present application disclose the invention including the following aspect relating to a technique for automatically extracting a tumor from nuclear medicine image data. This aspect of the invention is characterized in that it includes:

acquiring a pixel group of a region corresponding to a bone from a pixel group included in the nuclear medicine image data;

obtaining a standard deviation based on pixel values of at least a part of the acquired pixel group; and extracting a bone tumor pixel group based on the standard deviation.

The above aspect of the invention statistically extracts a bone tumor pixel group. This configuration reduces the variation in the results of extraction performed by different operators, enabling subjective extraction of tumors.

The above aspect of the invention is also applicable to both two-dimensional nuclear medicine image data and three-dimensional nuclear medicine image data.

For observing a tumor with three-dimensional bone scintigrams, the contour of the tumor may need to be extracted three-dimensionally. Conventional techniques for this extraction include a method of displaying nuclear medicine image data on a display and tracing the contour of the tumor with a mouse or other means to extract the tumor contour, and a method of specifying a range including the tumor in advance, setting an appropriate pixel threshold, and determining, to be the tumor contour, the boarder where pixel values exceed the threshold.

In the case of the former method, however, the shape of the extracted tumor varies depending on the skill or preference of an operator. Furthermore, three-dimensionally extracting a contour manually is a complex task, which requires effort of an operator. The shape of the contour varies depending on the operator. In the case of the latter method, the detected tumor contour may change depending on the set threshold.

In view of solving such a problem, the inventors of the present application disclose the invention including the following aspect relating to a technique for automatically extracting the contour of a tumor from nuclear medicine image data. This aspect of the invention is characterized in that it includes:

setting a reference point in a region including a tumor on the nuclear medicine image data;

scanning pixels radially and three-dimensionally from the reference point, and creating a pixel value profile in each scanning direction;

creating a gradient strength profile for the pixel value profile or for the pixel value profile to which smoothing has been applied;

setting a contour identification range in the pixel value profile or in the pixel value profile to which smoothing has been applied; and determining a tumor contour point in the pixel value profile within the contour identification range, based on a peak having the largest kurtosis in the corresponding gradient strength profile or in the corresponding gradient strength profile to which smoothing has been applied.

The above aspect of the invention automatically extracts the contour of a tumor. This configuration reduces the variation in the results of extraction performed by different operators, enabling subjective extraction of tumor contours. In addition, automatic extraction of contours significantly reduces the effort of operators.

An example of preferred embodiments of the invention disclosed in the description of the present application is characterized in that it includes:

extracting a bone region from CT image data that has been aligned with nuclear medicine image data;

displaying, from among the nuclear medicine image data, data of a region overlapping the extracted bone region; and not displaying, from among the nuclear medicine image data, data of a region not overlapping the extracted bone region.

Another example of preferred embodiments of the invention disclosed in the description of the present application is characterized in that it includes:

acquiring a pixel group of a region corresponding to a bone from a pixel group included in nuclear medicine image data;

obtaining a standard deviation based on pixel values of at least a part of the acquired pixel group; and extracting a bone tumor pixel group based on the standard deviation.

Another example of preferred embodiments of the present invention is characterized in that it includes:

setting a reference point in a region including a tumor on the nuclear medicine image data;

scanning pixels radially and three-dimensionally from the reference point, and creating a pixel value profile in each scanning direction;

creating a gradient strength profile for the pixel value profile or for the pixel value profile to which a smoothing has been applied;

setting a contour identification range in the pixel value profile or in the pixel value profile to which smoothing has been applied; and determining a tumor contour point in the pixel value profile within the contour identification range, based on a peak having the largest kurtosis in the corresponding gradient strength profile or in the corresponding gradient strength profile to which smoothing has been applied.

The invention of the present application may be embodied as, for example, a system including means for implementing at least one of the above features, a computer program that causes, when executed by processing means, the system to perform at least one of the above features, a method for implementing at least one of the above features, or any other forms.

Several preferred embodiments of the present invention are specified in the claims included in the attached claims. However, the embodiments specified in the claims do not necessarily include all the novel technical ideas disclosed in the present description and the drawings. The applicant claims to possess the right to have a patent granted on all the novel technical ideas disclosed in the present description and the drawings regardless of whether the novel technical ideas are claimed in the current claims.

BRIEF DESCRIPTION OF DRAWINGS

FIG. 3B is a diagram exemplifying an image obtained by additionally performing closing processing on the image in FIG. 3A.

FIG. 10A is a diagram exemplifying a process performed in step 722 for determining a tumor contour point.

DESCRIPTION OF EMBODIMENTS

Figure 1:
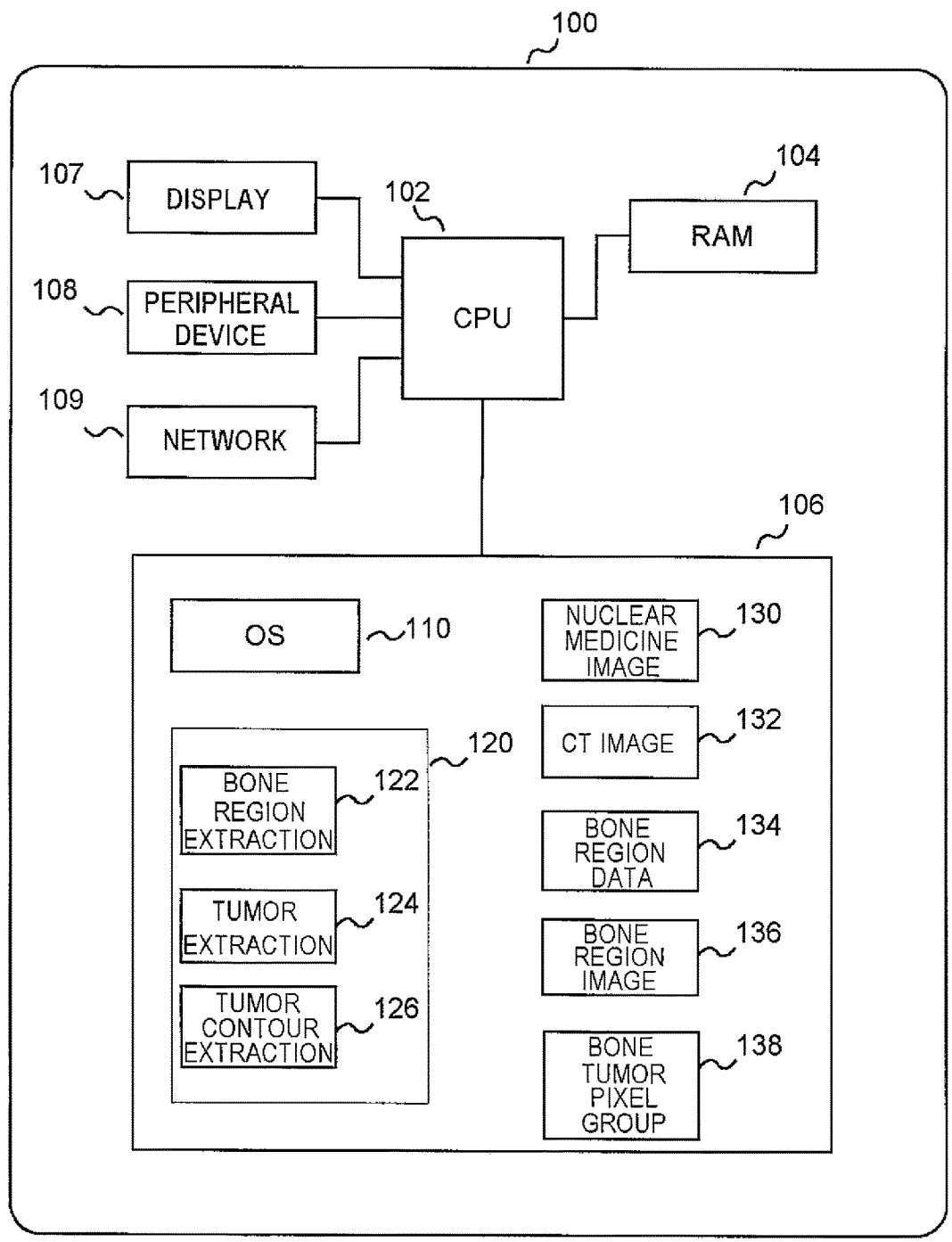
FIG. 1 is a diagram illustrating a main configuration of a system 100, which is exemplary hardware capable of executing various processes disclosed in the present description.

FIG. 1 is a diagram illustrating a main configuration of a system 100, which is exemplary hardware capable of executing various processes disclosed in the present description. As illustrated in FIG. 1, the system 100 is similar to a general-purpose computer in terms of hardware, and may include a central processing unit (CPU) 102, a main memory 104, a large-capacity storage unit 106, a display interface 107, a peripheral device interface 108, and a network interface 109, for example. Similarly to a general-purpose computer, a high-speed random access memory (RAM) may be used as the main memory 104, and an inexpensive, large-capacity hard disk or a solid state disk (SSD) may be used as the large-capacity storage unit 106. To the system 100, a display for displaying information may be connected through the display interface 107. Also to the system 100, a user interface such as a keyboard, a mouse, or a touch panel may be connected through the peripheral device interface 108. The network interface 109 may be used to connect the system 100 to another computer or the Internet via a network.

The large-capacity storage unit 106 may store therein, for example, an operating system (OS) 110 and a nuclear medicine image analysis program 120 for providing characteristic processes disclosed in the present description. The most basic functions of the system 100 are provided when the CPU 102 executes the OS 110. In addition, the characteristic processes disclosed in the present description are provided when the CPU 102 executes at least a part of a program instruction group contained in the nuclear medicine image analysis program 120. The characteristic processes disclosed in the present description can be roughly classified into the following three types: a process for removing physiological accumulation sites, a process for automatically extracting a tumor region, and a process for automatically extracting a tumor contour. The nuclear medicine image analysis program 120 may include program instruction groups or program modules 122, 124, and 126 to respectively execute the three types of processes. In some embodiments, each of these program instruction groups or program modules may be stored, copied, downloaded, or sold separately from other program instruction groups or program modules. In some embodiments, these program instruction groups or program modules may be inseparably integrated to form a single nuclear medicine image analysis program 120. As well known, embodiments of a computer program include various forms, and all of these forms are included in the scope of the invention disclosed in the present application.

The large-capacity storage unit 106 may further store therein, for example, nuclear medicine image data 130 subject to an analysis by the nuclear medicine image analysis program 120, computed tomography (CT) image data 132 corresponding to the nuclear medicine image data 130, and other pieces of data 134, 136, and 138.

Other than the components illustrated in FIG. 1, the system 100 may include the same units as those of a general computer system, such as a power source and a cooling unit. Various embodiments of a computer system employing various techniques have been known, such as distributed, redundant, or virtualized storage units, use of multiple CPUs, CPU virtualization, use of a processor specialized for a specific process such as digital signal processing (DSP), and implementation of a specific process as hardware to be used with a CPU. The invention disclosed in the present application may be implemented in any form of computer system. The form of computer system does not limit the scope of the invention. The technical ideas disclosed in the present description may generally be embodied as: (1) a computer program containing an instruction configured to cause, when executed by processing means, an apparatus or a system including the processing means to execute various processes described in the present description; (2) a method for operating the apparatus or the system, the method being performed when the processing means executes the computer program; and (3) the apparatus or the system including the computer program and the processing means configured to execute the computer program. As described above, part of software processing may be implemented as hardware.

Note that the pieces of data 130 to 138 are not stored in the large-capacity storage unit 106 in many cases at the time of manufacture, sales, and initial start-up of the system 100. These pieces of data may be transferred from an external apparatus to the system 100 through the peripheral device interface 108 or the network interface 109, for example. In some embodiments, the pieces of data 134 and 138 may be generated when the CPU 102 executes the computer program 120 or other computer programs. In some embodiments of the computer program 120 or the OS 110, the pieces of data 134 and 138 are stored only in the main memory 104 instead of being stored in the large-capacity storage unit 106. Note that the scope of the invention disclosed in the present application is not limited by the existence of the pieces of data 130 to 138.

The following describes the nuclear medicine image data 130 subject to processing in examples disclosed in the present description. The nuclear medicine image data 130 may be two-dimensional image data or three-dimensional image data acquired by, for example, a SPECT examination performed for evaluation of bone metastases of tumors or other purposes.

Specifically, for example, the nuclear medicine image data 130 may be two-dimensional image data or three-dimensional image data generated on the basis of radiation count values acquired by intravenously administering $^{99m}$Tc-HMDP as a radiopharmaceutical to a subject, and detecting radiation emitted from within the subject's body with a SPECT apparatus. In general, each pixel composing such an image has a value corresponding to a radioactivity count value; that is, each pixel value indicates the intensity of radioactivity.

Note that the data analyzable in the examples disclosed in the present description is not limited to SPECT image data. Various types of data are analyzable in the examples. For example, PET image data acquired by using $^{18}$F—NaF as a radiopharmaceutical is analyzable as well.

The CT image data 132 may be three-dimensional image data imaged by using X-ray CT on the same subject as that from which the nuclear medicine image data 130 has been created. Apparatuses that integrate SPECT and CT have recently been developed, thereby enabling imaging of CT images along with the execution of SPECT examination. The pieces of image data 130 and 132 may be imaged together by such an apparatus.

Figure 2:
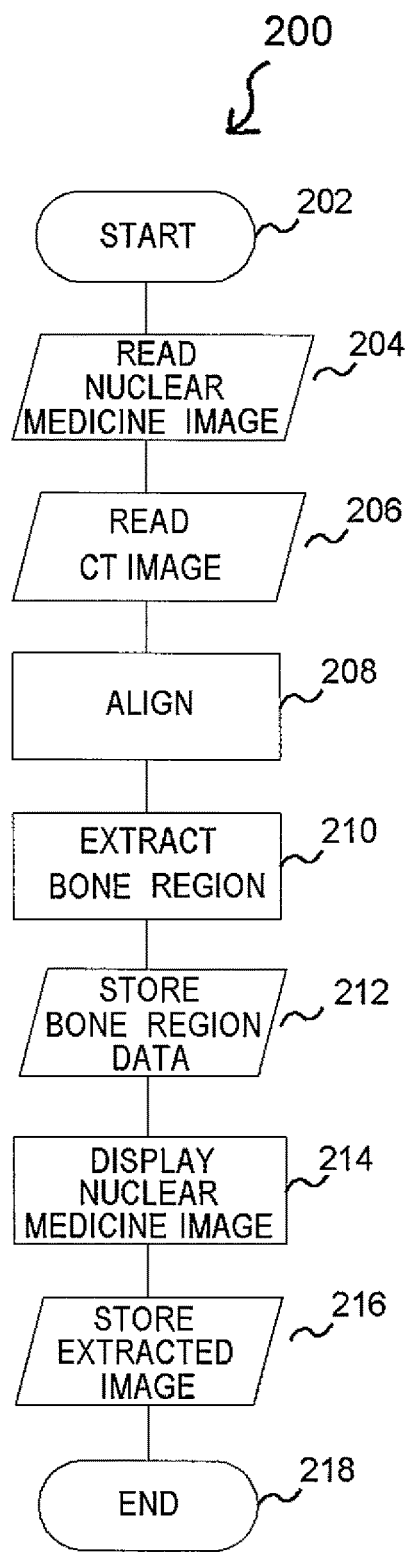
FIG. 2 is a flowchart illustrating a novel process 200 for extracting a bone region from nuclear medicine image data 130.

The following describes the characteristic processes disclosed in the present description with reference to FIG. 2 and following diagrams.

FIG. 2 is a flowchart illustrating a process 200 for extracting a bone region, disclosed in the present description. The process described in this flowchart may be performed by the system 100 when the CPU 102 executes, for example, the bone region extraction program module 122 of the nuclear medicine image analysis program 120.

Step 202 indicates the start of processing. In step 204, the three-dimensional nuclear medicine image data 130 subject to processing in the present example is read. For example, according to an instruction of the program instruction group contained in the nuclear medicine image analysis program 120, the CPU 102 copies at least part of the image data 130 from the large-capacity storage unit 106 to the main memory 104.

In one example, the nuclear medicine image data 130 that has been stored on a storage medium may be read with a dedicated reading apparatus and captured into the system 100 through the peripheral device interface 108. In another aspect, the nuclear medicine image data 130 may be captured through the network interface 109 as data signals superimposed on carrier waves. In another example, the captured nuclear Medicine image data 130 may be stored on the large-capacity storage unit 106 once and then copied to the main memory 104, or may be Stored directly on the main memory 104 and processed as it is.

In step 206, the CT image data 132 is read.

In step 208, co-registration of the nuclear medicine image data 130 and the CT image data 132 is performed. In other words, the orientations, sizes, and positions of the body are aligned three-dimensionally between the nuclear medicine image data 130 and the CT image data 132. This process enables comparison between the nuclear medicine image data 130 and the CT image data 132. This process may simply be called registration. Co-registration functions have been included in a number of nuclear medicine image data analysis programs available in the market. A known technique implemented in such analysis programs or other publicly known methods can be used to perform co-registration in the present example. Co-registration may be performed manually, that is, by displaying nuclear medicine image data and CT image data together as images, and moving one image in parallel with the other image or rotating one image, to align one image with the other image.

In some embodiments, the co-registration of the pieces of image data 130 and 132 may have been completed. For example, in a case where the pieces of image data 130 and 132 are imaged together by an apparatus that integrates SPECT or PET with CT, the co-registration of the nuclear medicine image data 130 and the CT image data 132 may have been completed by the time when the pieces of data are output from the apparatus. In this case, the process in step 208 is unnecessary.

In step 210, a bone region is three-dimensionally extracted using the CT image data 132. In some embodiments, this process may simply extract, from a CT image, a region having pixel values equal to or larger than a threshold, as a bone region. Simply performing extraction using a threshold, however, may leave out the inside of bone or generate noise. Thus, in some embodiments, closing processing by a publicly known method may be performed on the image data constructed with pixels having pixel values equal to or larger than a threshold, and the remaining pixels are set to be a bone region. Other noise removal methods may be used, such as a method of removing a volume including voxels the number of which is equal to or smaller than a certain threshold, and a method of removing manually specified noise.

A threshold used for extracting a bone region may be a value generally known to the skilled person in the field as a Hounsfield value that indicates a bone region. The present example uses 152.

Figure 3A:
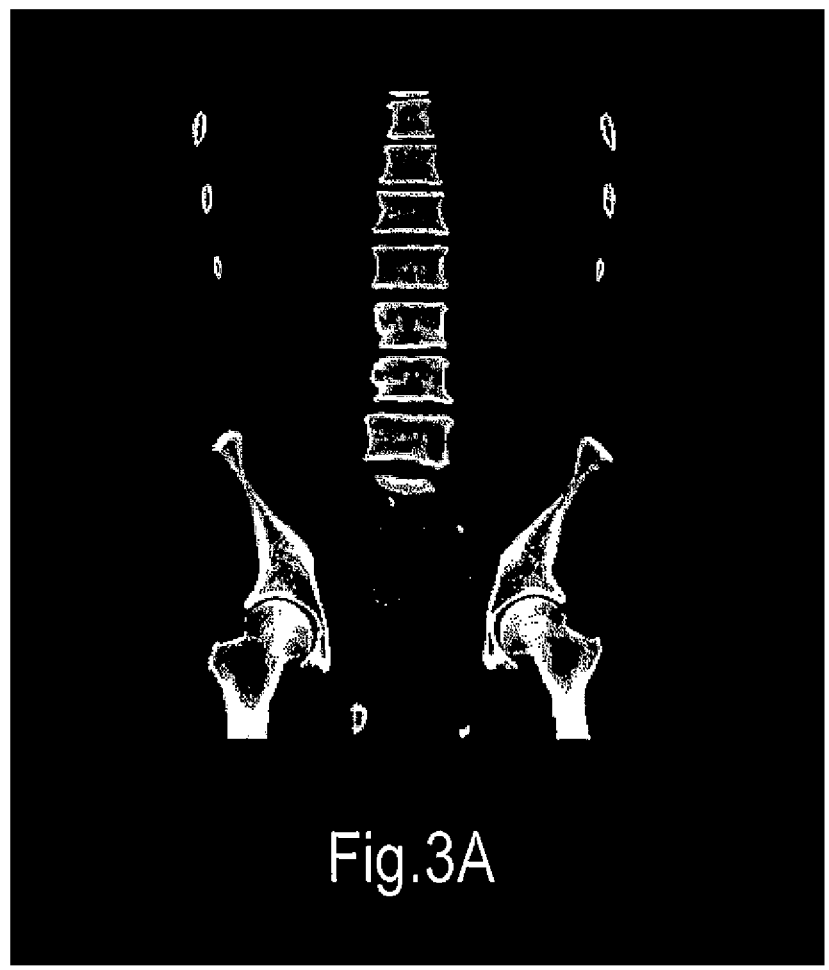
FIG. 3A is a diagram exemplifying a bone image created using the pixels simply extracted using a threshold in step 210.

FIG. 3A exemplifies a bone image created using the pixels simply extracted using a threshold. FIG. 3B exemplifies an image obtained by additionally performing closing processing on the image in FIG. 3A. As FIG. 3A illustrates, some inner parts of bones are displayed in black, indicating that some parts are not extracted as bone regions. In contrast, the image in FIG. 3B displays inner parts of bones and parts between vertebrae in white, indicating that the bone regions are more preferably extracted than those in FIG. 3A. Thus, the present example uses, as extracted bone regions, data obtained by additionally performing closing processing on an image data extracted using a threshold, that is, data that can be visualized as exemplified in FIG. 3B, for subsequent processing. Note that the present example sets the number of times the closing processing is performed to three. The extracted bone region data may be, for example, image data that contains a pixel value of one or larger for each pixel extracted as the bone region, and a pixel value assigned with zero or a null code for each pixel not extracted as the bone region. The extracted bone region data may be stored, for example, on the main memory 104, and/or, as the data 134 or other data, on the large-capacity storage unit 106 (step 212).

In step 210, it is preferable that a threshold used for extracting a bone region or the number of closing processes be optionally adjustable by a use. The nuclear medicine image analysis program 120 (or the bone region extraction program module 122) is preferably configured to allow such optional setting.

In step 214, the bone region data obtained in step 210 is used to display the nuclear medicine image data 130. Display processing performed in this step is characterized in that, from among the pixels contained in the nuclear medicine image data 130, the pixels overlapping the bone region extracted in step 210 are displayed, and the pixels not overlapping the bone region are not displayed. For example, with respect to each pixel in the nuclear medicine image data 130, the corresponding pixel in the bone region data 134 obtained in step 210 may be checked for the presence of an effective pixel value, which is not zero or a null code, and only if an effective value is present, the pixel in the nuclear medicine image data 130 corresponding to the pixel having the effective value in the bone region data 134 may be displayed (that is, pixels not contained in the bone region data 134 are not displayed). In another aspect, each pixel in the nuclear medicine image data 130, excluding the pixels corresponding to the bone region data 134 obtained in step 210, may be assigned with zero or a null code.

Figure 4A:
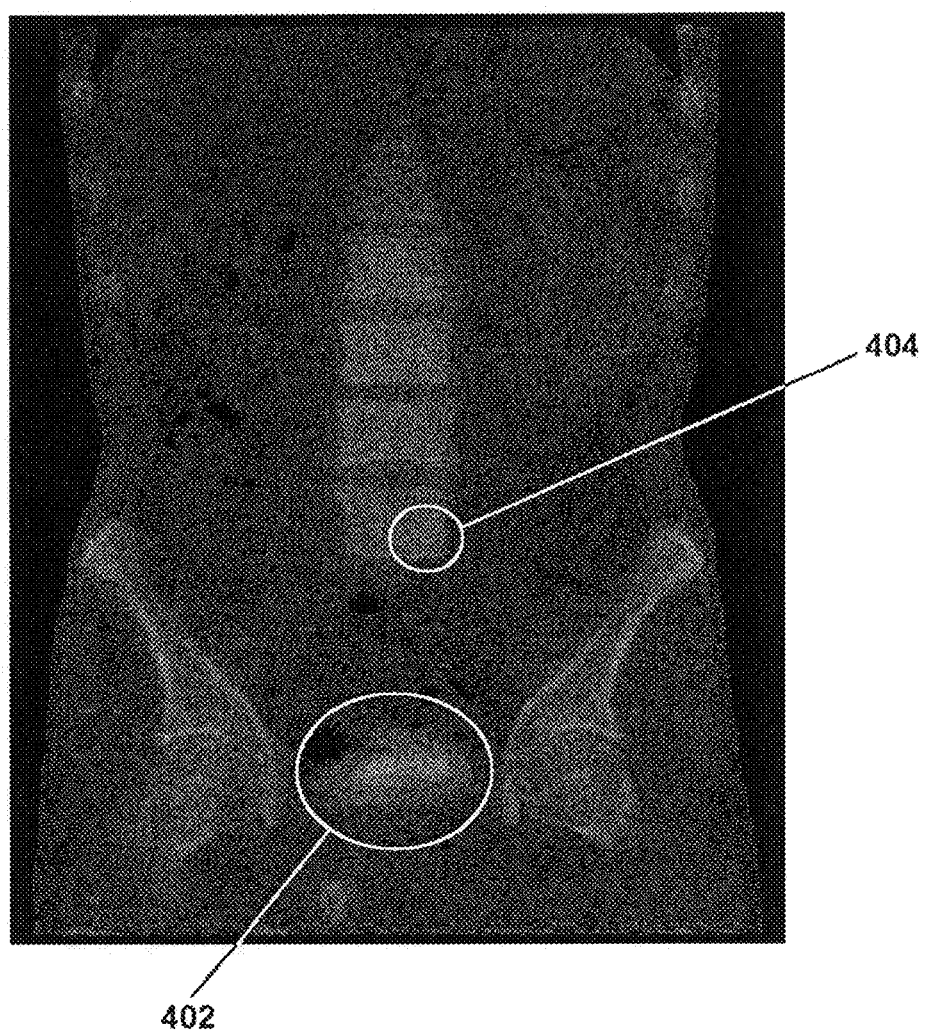
FIG. 4A is a diagram exemplifying a display performed in step 214.
Figure 4B:
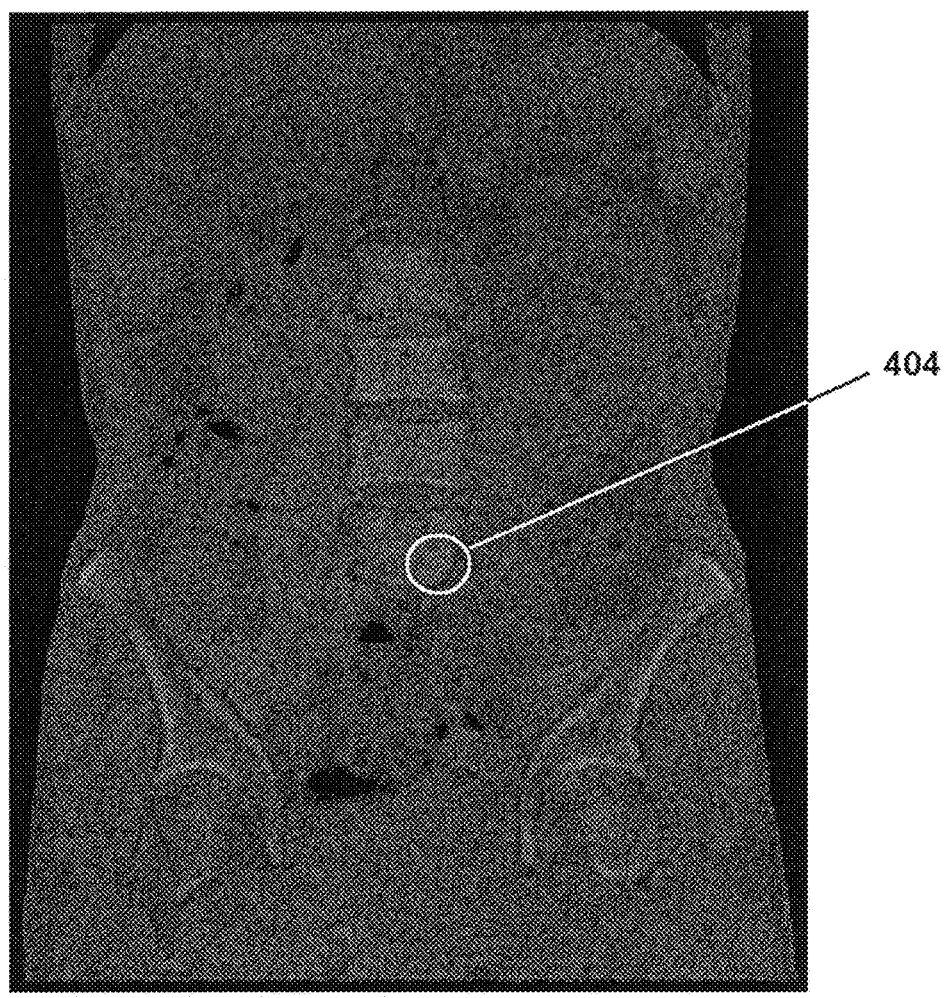
FIG. 4B is a diagram exemplifying a display performed in step 214.

The following exemplifies how the display in step 214 looks like with reference to FIG. 4A and FIG. 4B. FIG. 4A is an image of an appropriate section cut out of the CT image data 132, on which the same section cut out of the nuclear medicine image data 130 is superimposed. Accumulation of radioactivity can be observed at the locations denoted by symbols 402 and 404. (The location denoted by symbol 404 may be difficult to recognize due to the limitation that images in patent application documents need to be in black and white.) The location denoted by symbol 402 is, however, the bladder. That is, the reason for the accumulation of radioactivity is an excretory process, and not the presence of a lesion. In contrast, the accumulation observed at the location denoted by symbol 404 is probably due to the presence of a lesion.

FIG. 4B also illustrates the same CT image used in FIG. 4A, on which the corresponding section of the nuclear medicine image data 130 is superimposed. The pixels displayed in the nuclear medicine image data, however, are only the pixels overlapping the bone region extracted in step 210. As is obvious from the drawing, no accumulation of radioactivity is displayed in the region of the kidneys or the bladder. In contrast, the accumulation observed at the location denoted by symbol 404 still remains. This means that, in FIG. 4B, an accumulation due to a physiological reason hardly appears on the displayed nuclear medicine image, whereas an accumulation due to a lesion clearly appears on the displayed nuclear medicine image. Thus, the above process enables observation and analysis of nuclear medicine image data with the effect of accumulation due to normal physiological reasons excluded.

Regarding the above process, Non Patent Literature 1 described below discloses a technique to detect an abnormal site from a CT image on the basis of a normal model constructed with a plurality of CT images. However, no technique has been disclosed that extracts a bone region from nuclear medicine image data to detect a tumor site with precision. Furthermore, no method has ever been disclosed for effectively removing physiological accumulation sites. Non Patent Literature 1: Xiangrong ZHOU, Hiroshi FUJITA, "Anatomical Structure Recognition of Normal Torso Region in Non-contrast CT Images", MEDICAL IMAGING TECHNOLOGY, Vol. 24, No. 3, May 2006, pp. 167-172

The difference between FIG. 4A and FIG. 4B is further highlighted when displayed in color, allowing highly clear observation of nuclear medicine information only in the bone regions. (Although FIG. 4A and FIG. 4B are actually color images, they are displayed in black and white due to the limitation in the number of colors usable in the drawings for patent application.) Note that FIG. 4A, FIG. 4B, FIG. 3A, and FIG. 3B each are an image created by a section of three-dimensional image data. The nuclear medicine image data 130 and the CT image data 132 are three-dimensional image data.

Image data may be displayed by transmitting, through the display interface 107, digital or analog signals for displaying the image data to a display device connected to the display interface 107. Thus, it should be noted that the word "to display" used in the description and the claims in the present application includes not only actually displaying on a display device but also generating digital or analog signals for displaying an image on the display device.

Nuclear medicine image data superimposed on the CT image in FIG. 4B is image data in which only the pixels overlapping the bone regions each have an effective pixel value (not zero or null code, for example) and the pixels not overlapping the bone regions are each assigned with a pixel value such as zero or a null code. In some embodiments, such image data may be stored, as the bone region nuclear medicine image data 136 for example, on the large-capacity storage unit 106 for example (step 216).

Step 218 indicates the end of processing.

Figure 5:
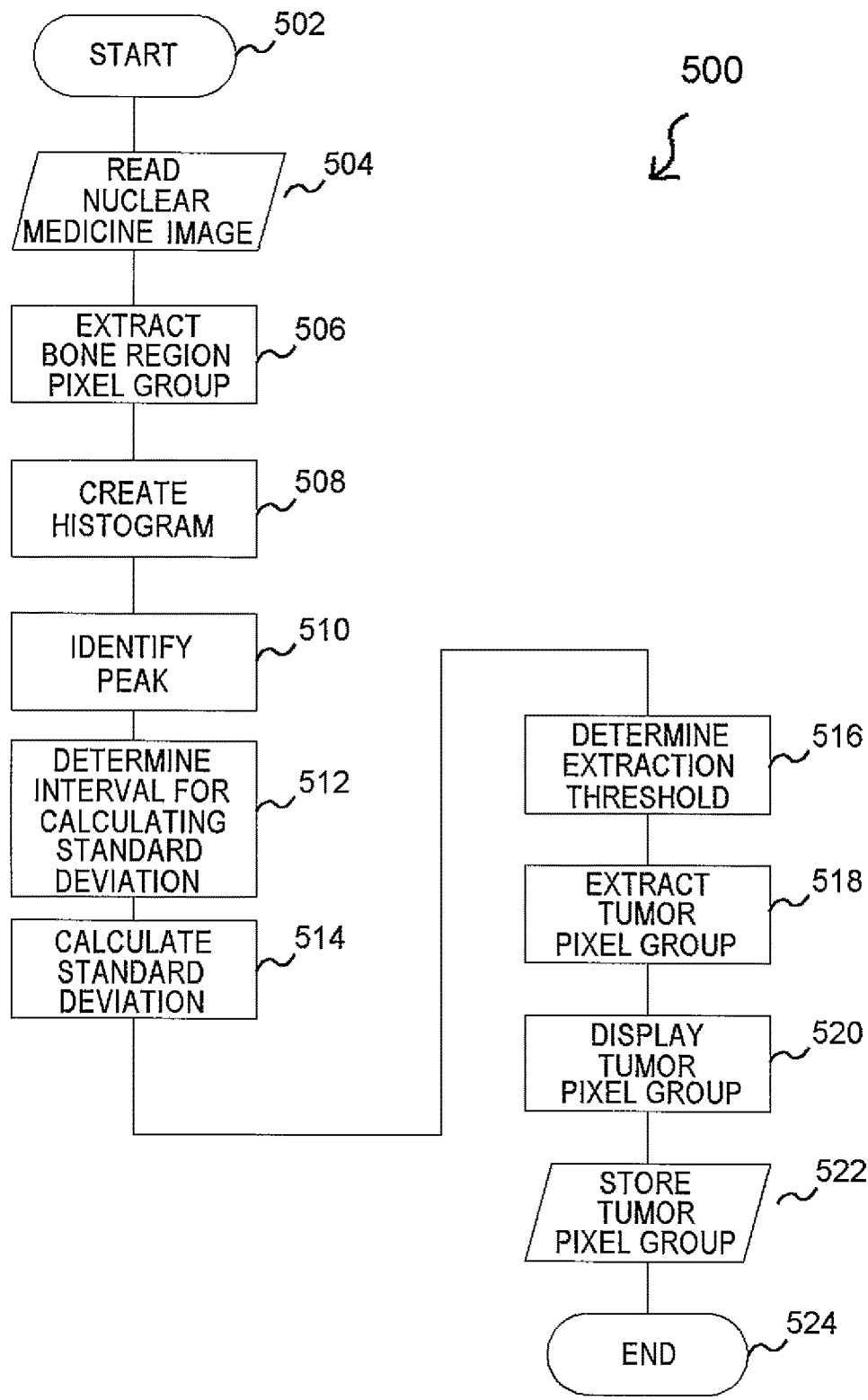
FIG. 5 is a flowchart illustrating a novel process 500 for automatically extracting a tumor from nuclear medicine image data.

The following describes a novel process for automatically extracting a tumor from nuclear medicine image data, with reference to FIG. 5.

FIG. 5 is a flowchart illustrating a process 500 for extracting a tumor from the nuclear medicine image data 130 disclosed in the present description. The process described in this flowchart may be performed by the system 100 when the CPU 102 executes, for example, the tumor extraction program module 124 of the nuclear medicine image analysis program 120.

Step 502 indicates the start of processing. In step 504, the three-dimensional nuclear medicine image data 130 subject to the process 500 is read. In step 506, a pixel group of a region corresponding to a bone is acquired from the nuclear medicine image data 130. In some embodiments, this process may be the process 200 itself described with reference to FIG. 2. Thus, in some embodiments, step 506 may be reading the bone region nuclear medicine image data 136 stored in step 216 of the process 200, from storage means (the large-capacity storage unit 106, for example).

In step 508, a histogram is created on the basis of the pixel values of the pixel group acquired in step 506. In some embodiments, a histogram of the pixel values as they are may be created. The pixel values of the pixels in the image data 130, however, generally indicate count values of radiation. Such pixel values are subject to change depending on the weight of a subject or an administered radioactivity dose, and thus vary among measurements. In a preferred embodiment of this step, it is preferable that the pixel values be converted to normalized values such as standardized uptake values (SUVs), and then a histogram of the SUVs or other values is created. This is because the SUV is a normalized value, which takes substantially the same value with respect to similar tissues regardless of measurement conditions. The SUV is, as well known in the field of the present application, a value defined as follows: SUV={Amount of attenuation-corrected radioactivity in region of interest (kBq) div Volume of region of interest (ml)}/{Administered radioactivity dose (MBq) div Body weight of subject (kg)}

Thus, the SUV is a value obtained by normalizing the radioactivity concentration in a region of interest with the administered radioactivity dose per kg body weight. The SUV can be an indicator that reflects the uptake of radioactivity or a radiopharmaceutical.

In step 510, the peak value is determined in the created histogram. That is, the largest frequency is determined. In step 512, a, class value having a frequency of a certain percentage of the peak value is determined in the created histogram. For example, a class value having a frequency of 5% of the peak value is determined. That is, two class values having a frequency of 5% of the peak value are determined, one is located before and the other is located after the class value presenting the peak value. In step 512, the interval defined by the two class values is determined to be the interval in which the standard deviation is calculated in the next step.

In step 514, the standard deviation of the class values included in the interval determined in step 512 is calculated.

In step 516, a threshold used to extract a tumor pixel group is determined. A threshold T calculated in step 516 may be represented by the following formula:

$$T = \text{BaseValue} + \alpha \cdot \text{SD},$$

where BaseValue is the larger one of the two class values calculated in step 512, SD is the standard deviation calculated in step 514, and α is a constant. A large α decreases the number of pixels extracted as tumor pixels, while a small α increases the number of extracted pixels. Thus, it is preferable that the value of α, be adjustable according to the difference in nuclear medicine examination apparatuses and the preferences of doctors. It is preferable that the nuclear medicine image analysis program 120 (or the tumor extraction program module 124) be configured to allow the optional setting of α. However, studies performed by the inventors of the present application have revealed that setting α to 0.5 yields an appropriated result in many cases.

In step 518, the pixels having the pixel values or the SUVs, which have been calculated on the basis of the respective pixel values, equal to or larger than the threshold determined in step 516, are extracted as a pixel group (a bone tumor pixel group) of a region in which a bone tumor may possibly be present.

Figure 6:
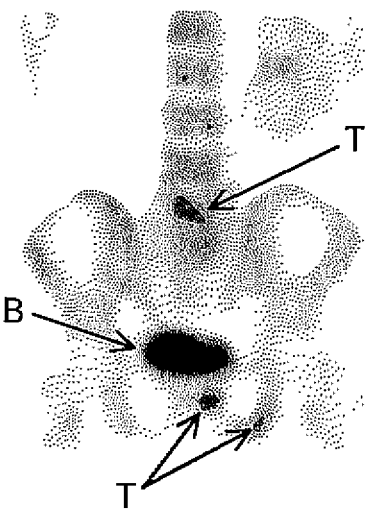
FIG. 6 is a diagram exemplifying a display of a bone tumor pixel group extracted in step 518.

In step 520, the bone tumor pixel group extracted in step 518 is displayed. FIG. 6 illustrates an example of the display. FIG. 6 is an image of an appropriate section cut out of the three-dimensional nuclear medicine image data 130, on which bone tumor pixel groups located on the section are superimposed.

In FIG. 6, the locations denoted by symbols T and displayed in a dark color are the extracted bone tumor pixel groups. Although the location denoted by symbol B is also displayed in a dark color, it is the pixel group corresponding to the bladder, which is displayed dark due to physiological accumulation of radioactivity. Pixel groups corresponding to physiological accumulation sites in the kidneys, the bladder, and other sites are not included in the bone region pixel groups extracted in step 506, and thus they are not extracted as tumors in step 518. In an actually used embodiment, the bone tumor pixel groups T are preferably displayed in a color clearly different from that of the physiological accumulation pixel group B so that the bone tumor pixel groups can be clearly identified. FIG. 6 was originally created as a color image. The section of the nuclear medicine image data 130 including the physiological accumulation pixel group B is displayed in grayscale, and the bone tumor pixel groups T is displayed in red. FIG. 6 has been converted to a black and white image due to the limitation in the number of colors usable in the drawings for patent application.

The above process statistically extracts a bone tumor pixel group using a histogram and the standard deviation. This configuration reduces the variation in the results of extraction performed by different operators, enabling subjective extraction of tumors. In addition, optional setting of α enables flexible setting according to requests of operators.

Note that, in the present example, the processing in step 506 to step 518 is performed three-dimensionally. In other words, the bone region pixel group extracted in step 506 spreads three-dimensionally. The standard deviation calculated in step 514 is the standard deviation of the pixel values of the bone region pixel group that spreads three-dimensionally. The bone tumor pixel group extracted in step 518 also spreads three-dimensionally. The sectional view illustrated in FIG. 6 represents merely a section of the three-dimensional spread.

In some embodiments, however, the processing in step 506 to step 518 may be performed two-dimensionally using data of a specific section of the three-dimensional nuclear medicine image data 130.

In some embodiments, a threshold set in step 516 may be given by the following formula:

Threshold=Mean+β·Standard Deviation, where the standard deviation is the value calculated in step 514 and the mean is the mean value inevitably calculated in the calculation of the standard deviation. In some embodiments, the threshold may be set on the basis of the mean and the standard deviation described above calculated using all the pixel groups extracted in step 506. Furthermore, in some embodiments, the threshold may be set on the basis of the mean and the standard deviation described above calculated using original pixel values that have not been converted to the SUVs. The inventors of the present application have found that a tumor pixel group may preferably be extracted with a threshold set by any of the above described methods. Note that β is a positive number that can optionally be set by a user. The inventors of the present application have found that a tumor pixel group can preferably be extracted by setting β to 1 in many cases.

In some embodiments, the data of the bone tumor pixel group extracted in step 518 may be stored. Such data may be stored, as the bone tumor pixel group data 138 for example, on the large-capacity storage unit 106 for example (step 522). Step 524 indicates the end of processing.

Figure 7A:
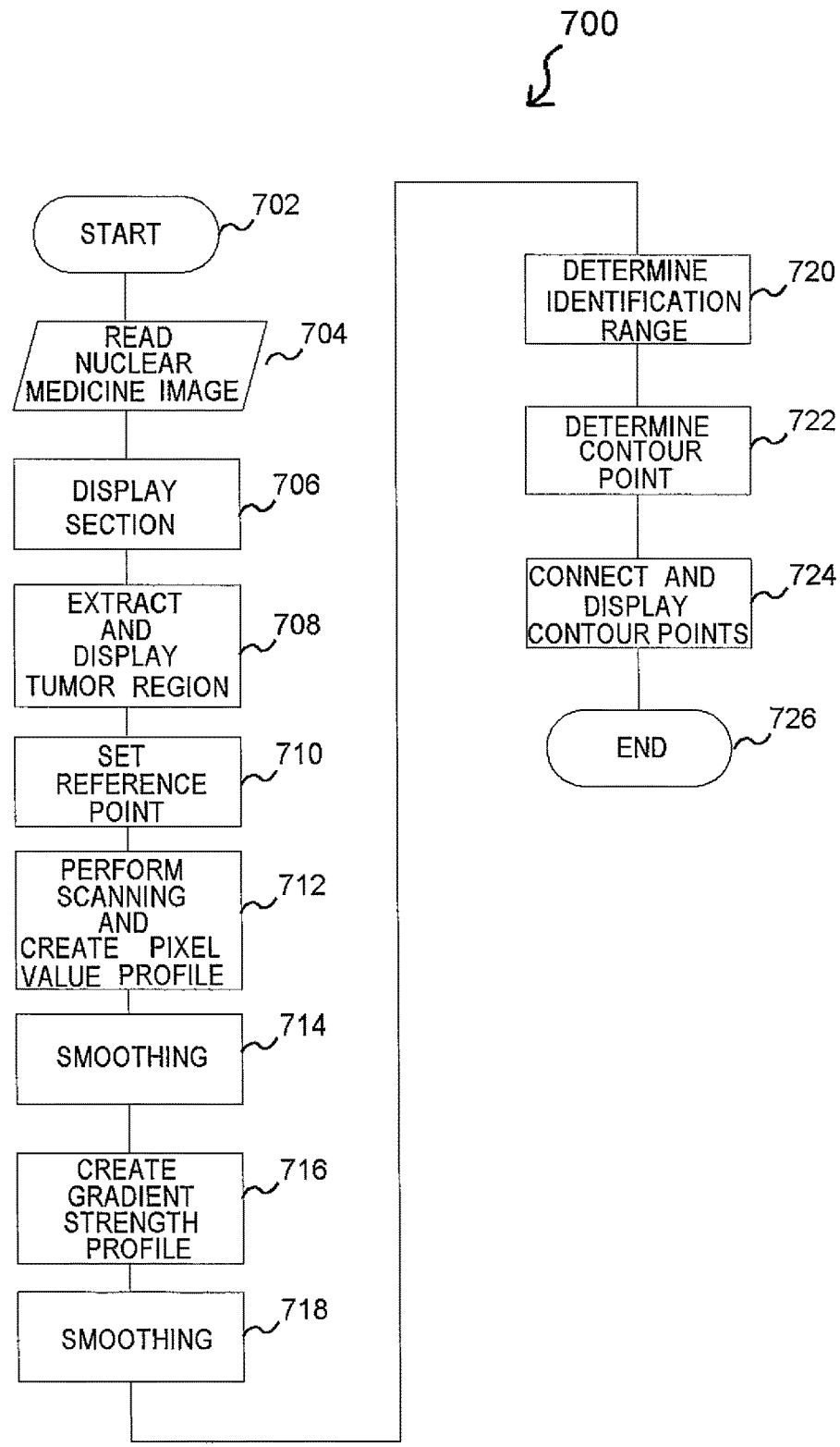
FIG. 7A is a flowchart illustrating a novel process 700 for automatically extracting the contour of a tumor from nuclear medicine image data.

The following describes a novel process for automatically extracting the contour of a tumor from nuclear medicine image data, with reference to FIG. 7A.

FIG. 7A is a flowchart illustrating a process 700 for extracting a tumor contour from the nuclear medicine image data 130 disclosed in the present description. The process described in this flowchart may be performed by the system 100 when the CPU 102 executes, for example, the tumor contour extraction program module 126 of the nuclear medicine image analysis program 120.

Step 702 indicates the start of processing. In step 704, the nuclear medicine image data 130 subject to the process 700 is read. In step 706, an appropriate sectional image is cut out of the nuclear medicine image data 130 and is displayed on a display device.

In step 708, a region including a tumor is highlighted on the sectional image displayed in step 706. In order to perform this processing, the region including the tumor needs to be extracted from the nuclear medicine image data 130. This extraction processing can be performed by several methods. One of the methods may be the process 500 itself described with reference to FIG. 5. Thus, in some embodiments, the bone tumor pixel group data 138 stored in step 522 of the process 500 may be read from storage means (the large-capacity storage unit 106, for example) in step 706. Subsequently, a pixel group in the bone tumor pixel group data 138, which is located on the section displayed in step 706, may be displayed identifiably (in a color different from that of the sectional image displayed in step 706, for example).

Another example of the methods for extracting a region including a tumor from the nuclear medicine image data 130, which should be performed in step 708, is to extract, as a region including a tumor, a pixel group having pixel values equal to or larger than a certain threshold from the nuclear medicine image data 130. Still another example of the methods is that an operator visually identifies a region including a tumor and specifies the region by an operation such as circling the region with a mouse. Any of the above described methods may be implemented according to an embodiment to extract a region including a tumor from the nuclear medicine image data 130. Alternatively, a method different from the three methods may be used to extract a tumor region. In any of the methods, the extracted tumor region is preferably displayed on a display in a form readily identifiable by an operator.

Figure 8A:
FIG. 8A is a diagram exemplifying a display performed in step 708.

FIG. 8A exemplifies a display performed in step 708. As illustrated in FIG. 8A, a region is displayed in a dark color on a sectional image of the nuclear medicine image data 130. The region displayed in a dark color denoted by symbol 802 is the tumor region. FIG. 8A should preferably be a color image. The color used for the tumor region is preferably a color clearly different from the color used for the sectional image of the nuclear medicine image data 130. (FIG. 8A is originally a color image and the region denoted by symbol 802 is painted in red.) The tumor region exemplified in FIG. 8A is the region extracted by the embodiment of the process 500 described with reference to FIG. 5. (Physiological accumulation sites of radiopharmaceuticals have also been removed by the embodiment of the process 200 described with reference to FIG. 2. This explains the reason that no accumulation is observed in the site corresponding to the bladder.)

The sectional image displayed in step 706 may be a sectional image including a tumor region automatically extracted by the system 100. The method for automatically extracting a tumor region may be, for example, one of the methods described in relation to step 708. In some embodiments, the processing performed in step 706 and the processing performed in step 708 may be performed in a partly reversed order (to the order indicated in FIG. 7A) or performed integrally. The system 100 may be configured to automatically select, as a section to display in step 706, a section including the center coordinates of an automatically extracted tumor region or a section including pixels each having the largest pixel value in the tumor region, for example. The system 100 may also be configured to, when a plurality of tumor regions have automatically been extracted, automatically select a section including a tumor having the largest volume, as a section to display in step 706. The system 100 may also be configured to, when a plurality of tumor regions have automatically been extracted, display a list of the tumor regions to allow a user to select a tumor region. According to a selection by the user, the system 100 may display a section including the selected tumor region. The system 100 may also be configured to allow a user to select or change a sectional image to display in step 706. For example, a user interface element such as a scroll bar may be used to allow a user to optionally perform selection or change.

In step 710, a reference point is set in the displayed tumor region. The reference point is a point of reference for pixel scanning to be performed in the next step. A reference point can be set by several methods depending on embodiments. One of the methods is to set a reference point on the basis of selection operation performed by an operator. For example, when an operator clicks with a mouse on any point in the tumor region displayed in step 708 on a display device, the system 100 may set the pixel in the nuclear medicine image data 130 corresponding to the clicked position to be the reference point. It is clear that similar processing is possible with other input means than a mouse.

In some embodiments, the system 100 may be configured to automatically set the reference point. For example, the center coordinates of a tumor region or a pixel having the largest pixel value in a tumor region may be set to be the reference point.

In an embodiment, the following process is performed to set the reference point automatically.
(1) The image data 130 is copied.
(2) A tumor region is automatically extracted from the copied image data, and all the pixel values excluding those of the extracted tumor region are set to null in the copied image data. The method for extracting a tumor region may be, for example, one of the methods described in relation to step 708.
(3) A section including a pixel having the largest pixel value in the automatically extracted tumor region is cut out.
(4) In the tumor region included in the section, two end points are set. The first end point is a pixel having the smallest coordinate value on one axis (x axis, for example). The second end point is a pixel having the largest coordinate value on the same axis.
(5) A pixel located at the midpoint between the first end point and the second end point is set to be a candidate reference point.
(6) If the pixel value of the pixel set to be the candidate reference point is not null, the pixel is determined to be the final reference point.
(7) If the pixel value of the pixel set to be the candidate reference point is null, the process returns to (4) and shifts the first end point or the second end point by a certain amount (by one pixel, for example) in the tumor region, and proceeds to (5) and the following steps again.

In the process 700, where to set a reference point does not significantly affect the quality of the final result of an extracted tumor contour. The reference point is, however, preferably set within a tumor region.

When a plurality of tumor regions are present in the displayed sectional image, a plurality of reference points are set for the respective tumor regions.

Figure 8B:
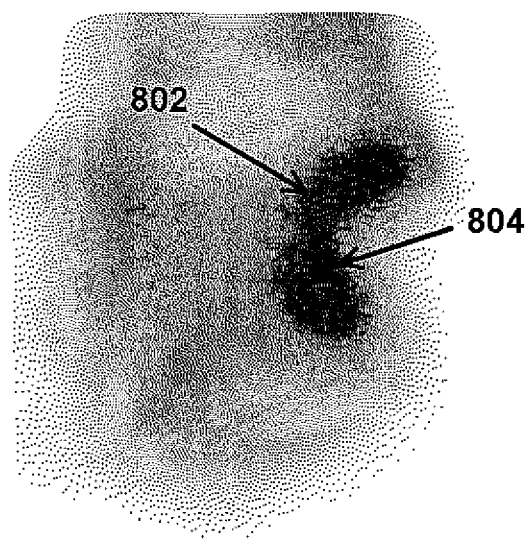
FIG. 8B is a diagram exemplifying a reference point set in step 710.

FIG. 8B exemplifies a reference point set in step 710. The dark colored region denoted by symbol 802 is the same region as the tumor region in FIG. 8A. In this example, a reference point is set at the position of the black point denoted by symbol 804.

Figure 8C:
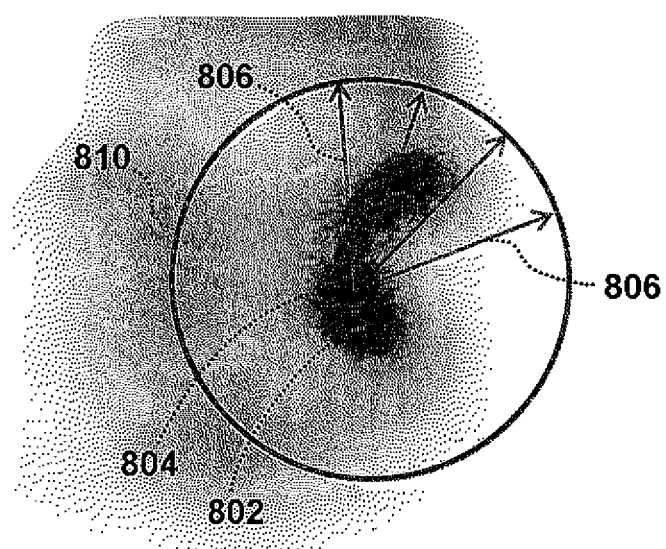
FIG. 8C is a diagram illustrating scanning performed in step 712.

In step 712, the nuclear medicine image data 130 is scanned radially and three-dimensionally starting from the reference point, and the change in pixel values in each scanning direction is checked to create a profile of pixel values. FIG. 8C illustrates this process. Each of the four arrows 806 drawn from the reference point 804 indicates one scanning direction. Although only four scanning directions are illustrated in FIG. 8C, scanning should be performed radially and three-dimensionally in every direction in practice. In an example of contour extraction to be described later, scanning in the same plane is performed by 1° in all directions for 360° around the reference point. The plane to be scanned is rotated by 1° for 180° around an axis passing through the reference point, each plane being scanned in all directions, for extracting a contour. Thus, the above process creates 360×180=64800 pixel value profiles in total. It is needless to say that these values are merely examples and the degree units may differ from the above described values.

The circle denoted by symbol 810 indicates a scanning range on a specific plane. That is, pixel values are scanned in each direction in the plane within the range of the reference point to the circle 810. Limiting the scanning range as described above prevents waste of computing resources due to scanning of unnecessary ranges. In this example, pixel values are sampled at 26 points from the reference point to the circle 810 in each scanning direction. A scanning range is preferably set to include an entire tumor region. The number of samples described above is merely an example.

Figure 8D:
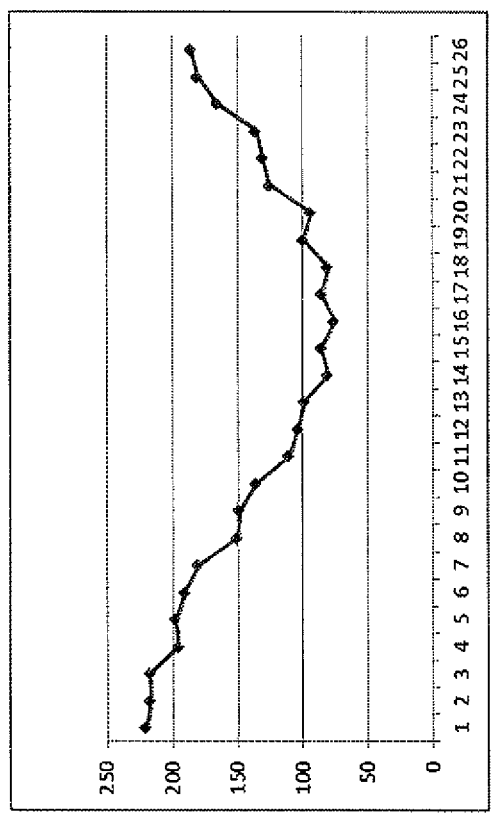
FIG. 8D is an example of pixel profiles created in step 712.

FIG. 8D exemplifies a pixel value profile created on one of the scanning directions. The values on the abscissa axis correspond to the positions of the sampling points. As described above, 26 points have been sampled in this example, and thus 26 points are plotted in FIG. 8D. The values on the ordinate axis are pixel values.

Figure 8E:
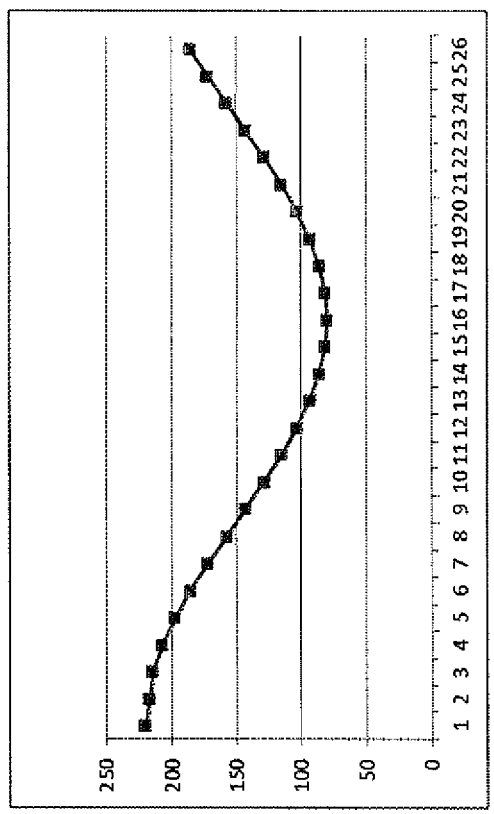
FIG. 8E is a diagram exemplifying smoothing performed in step 714.

In step 714, each of the pixel value profiles created in the previous step is processed by smoothing. Any method of smoothing may be used. For example, the well-known three-point moving average method may be used for smoothing. In other words, smoothing may be performed by replacing a pixel value at a sampling point with the averaged value among the pixel values at the three points, namely, the sampling point, and the previous and the next points to the sampling point. Various other smoothing methods may be applied depending on the embodiment. FIG. 8E illustrates the pixel value profile illustrated in FIG. 8D that has been smoothed by the three-point moving average method described above (in FIG. 8E, the values at both ends are remained as their original data values because the average of three points is not available for the end values).

Figure 8F:
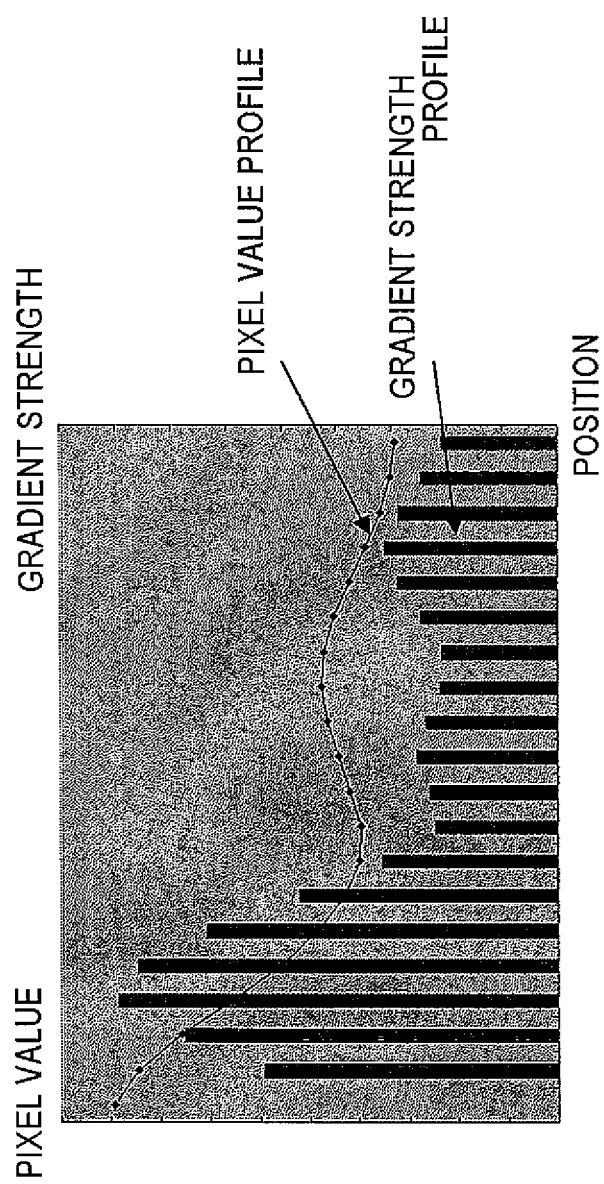
FIG. 8F is an example of gradient strength profiles created in step 716.

In step 716, a gradient strength profile is created for the smoothed pixel value profile. The gradient strength between a point 1 (x1, y1) and a point 2 (x2, y2) is defined by the square root of $\{(x2-x1)^2+(y2-y1)^2\}$. In this step, the gradient strength is calculated between each point in the pixel value profile smoothed in the previous step, and its adjacent point. Thus, in this example, a gradient strength profile including 25 gradient strength values is created for each pixel value profile including 26 pixel values. FIG. 8F illustrates a graph exemplifying a (smoothed) pixel value profile and the corresponding gradient strength profile.

In step 718, each of the gradient strength profiles created in the previous step is processed by smoothing. Similarly to the case where the pixel value profiles are processed by smoothing, any method of smoothing may be used. For example, the well-known three-point moving average method may be used for smoothing. This method is used to smooth the gradient strength profiles in this example as well.

In step 720, in each pixel value profile, a range (contour identification range) is determined in which a tumor contour point is identified. The contour identification range is determined on the basis of points that take extrema (extreme points) in the pixel value profile (or the pixel value profile smoothed in step 714). Extreme points can be searched for by, for example, calculating the differences between adjacent points in the pixel value profile (or the pixel value profile smoothed in step 714), and determining a point where the difference is zero or where the positive and negative signs are reversed, to be an extreme point. The contour identification range can be determined to be a range of, for example, the start point of the pixel value profile (or the pixel value profile smoothed in step 714) to the point determined to be the minimal value.

Figure 7B:
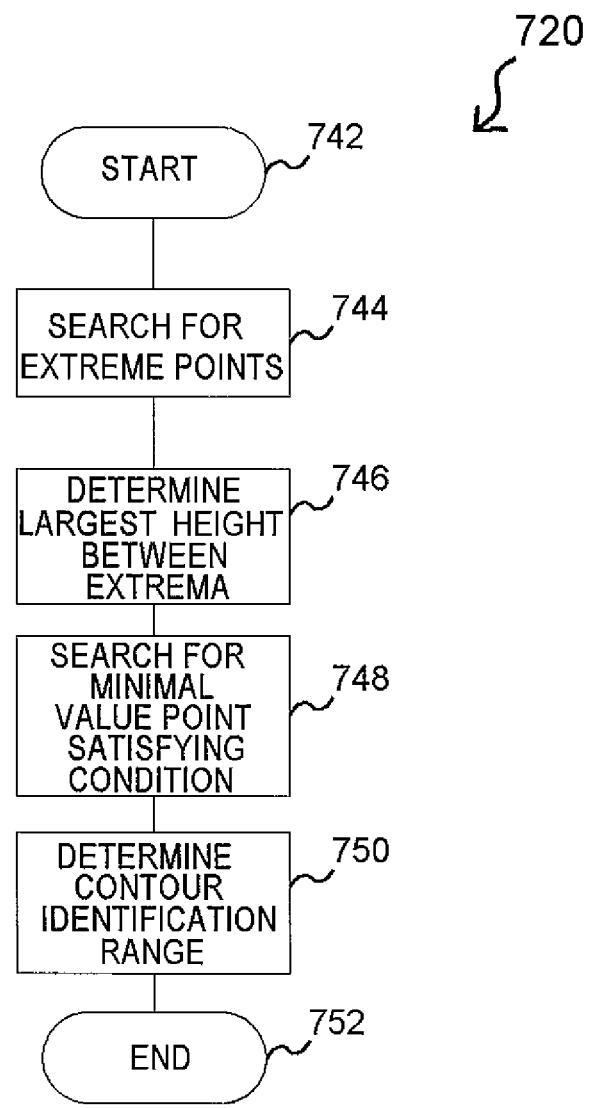
FIG. 7B is a flowchart exemplifying a process that can be performed in step 720.

The following exemplifies a process for determining a contour identification range that can be performed in step 720, with reference to FIG. 7B. Step 742 indicates the start of processing. In step 744, points that take extrema (extreme points) are searched for in the pixel value profile smoothed in step 714. In this searching, as described above, the difference between each of the points composing the smoothed pixel value profile and its adjacent point is calculated, and a point where the difference is zero or where the positive and negative signs are reversed can be determined to be an extreme point.

In step 746, the difference in pixel value is calculated among a plurality of detected extreme points to determine the maximum value of the difference.

In step 748, a minimal value point (that is, an extreme point that takes the minimal value) satisfying a certain condition is searched for among the extreme points detected in step 744. The minimal value point searched for here may be, for example, a minimal value having a difference from the immediately previous maximal value point (or maximum value point) of equal to or larger than 20% of the maximum value calculated in step 746, and may be the minimal value point closest to the reference point (the point set in step 710) (that is, the minimal value point having the smallest value on the abscissa axis).

In step 750, a contour identification range is determined. The contour identification range may be, for example, a range of the start point of the pixel value profile (that is, the point closest to the reference point) to the minimal value point specified in step 748.

Figure 9:
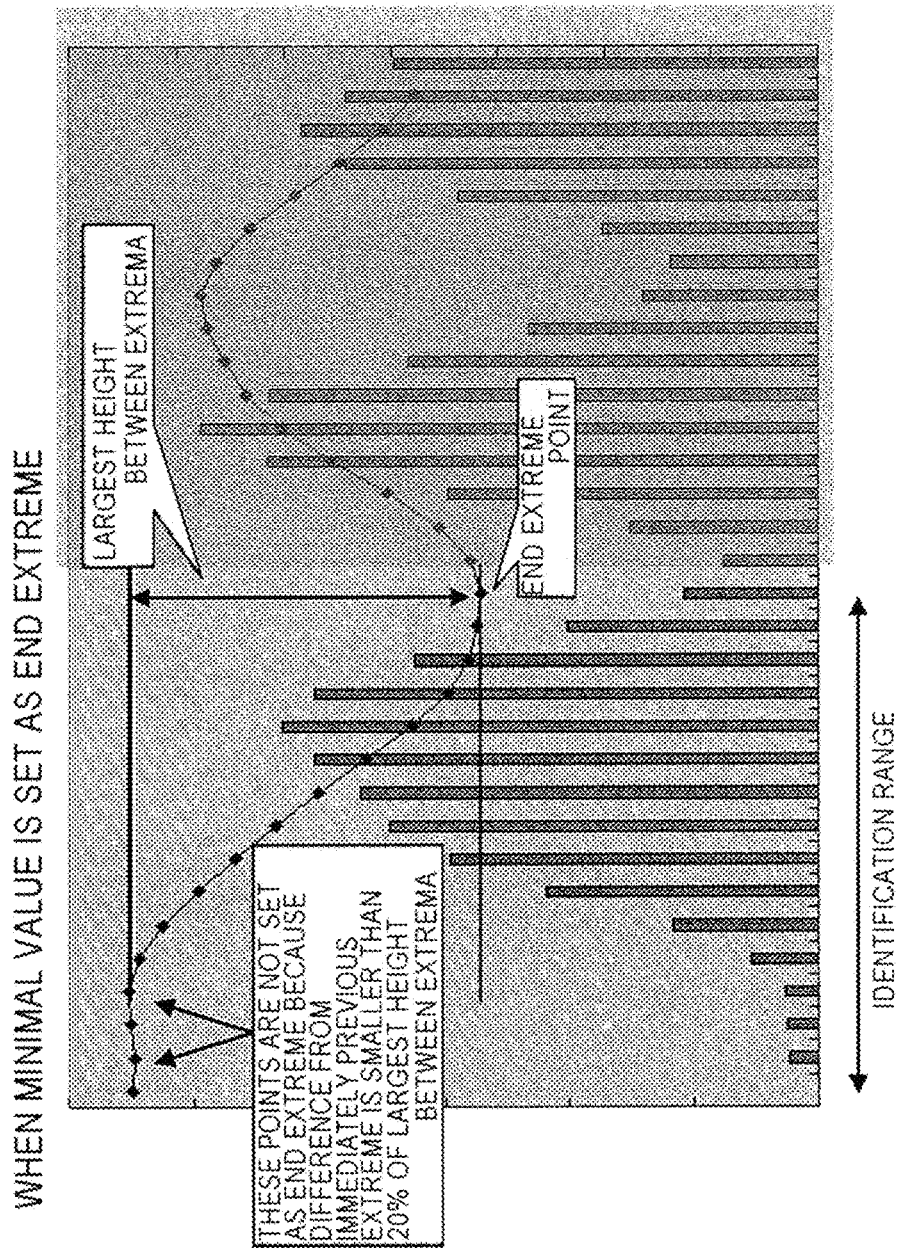
FIG. 9 is a diagram exemplifying a process performed in step 720 for determining a range in which a tumor contour point is identified.

FIG. 9 exemplifies the contour identification range determined in step 720.

Note that the above process for determining a contour identification range is an example. In some embodiments, a contour identification range may be determined by another method. For example, in some embodiments, a contour identification range may be determined by defining the point closest to the reference point to be the start point, and a point outwardly away from the tumor region extracted in step 708 by a certain distance (for example, a point located five pixels away from the tumor region outwardly) to be the end point, and defining the range between the start point and the end point to be the contour identification range.

In some embodiments, for example, the minimal value point specified in step 748 may be a minimal value point having the largest difference between extreme points (that is, a minimal value point that gives the maximum value obtained in step 746).

In some embodiments, for example, the start point of a contour identification range is a maximal value point closer to the reference point than the minimal value point specified in step 748, the maximal value point having a difference in pixel value from the minimal value point of, for example, equal to or larger than 20% of the maximum value calculated in step 746.

Note that specific processing for setting a contour identification range may vary depending on the embodiment. The value 20% used in the above description is merely an example, and other values may be used.

Returning back to FIG. 7A, the description of the process 700 is continued. In step 722, on the pixel value profile in which the contour identification range has been determined in step 720, a tumor contour point is determined using the smoothed gradient strength profile created in step 718. This step can proceed as follows, for example.

(Substep 1) Within the identification range set in step 720, a peak of the smoothed gradient strength profile is searched for. That is, an extreme point that gives the maximal value is searched for.

(Substep 2) If only one peak has been detected in substep 1, a point on the pixel value profile corresponding to the peak is determined to be a tumor contour point.

(Substep 3) If a plurality of peaks have been detected in substep 1, the kurtosis of each peak is calculated, and a point on the pixel value profile corresponding to the peak having the largest kurtosis is determined to be a tumor contour point. Here, the kurtosis is defined as the cosine (cos θ) of the angle (θ) between two vectors extending from the peak (maximal value point) to the respective adjacent minimal value points (extreme points that give minimal values). That is, the kurtosis cos (θ) can be defined as follows:

$$\cos\theta = \frac{x_1 \cdot x_2 + y_1 \cdot y_2}{\sqrt{x_1^2 + y_1^2} \cdot \sqrt{x_2^2 + y_2^2}}$$

where the direction vectors from the peak to the adjacent minimal value points are defined as follows:

$v1=\{x_1,y_1\}$ $v2=\{x_2,y_2\}$

Figure 10B:
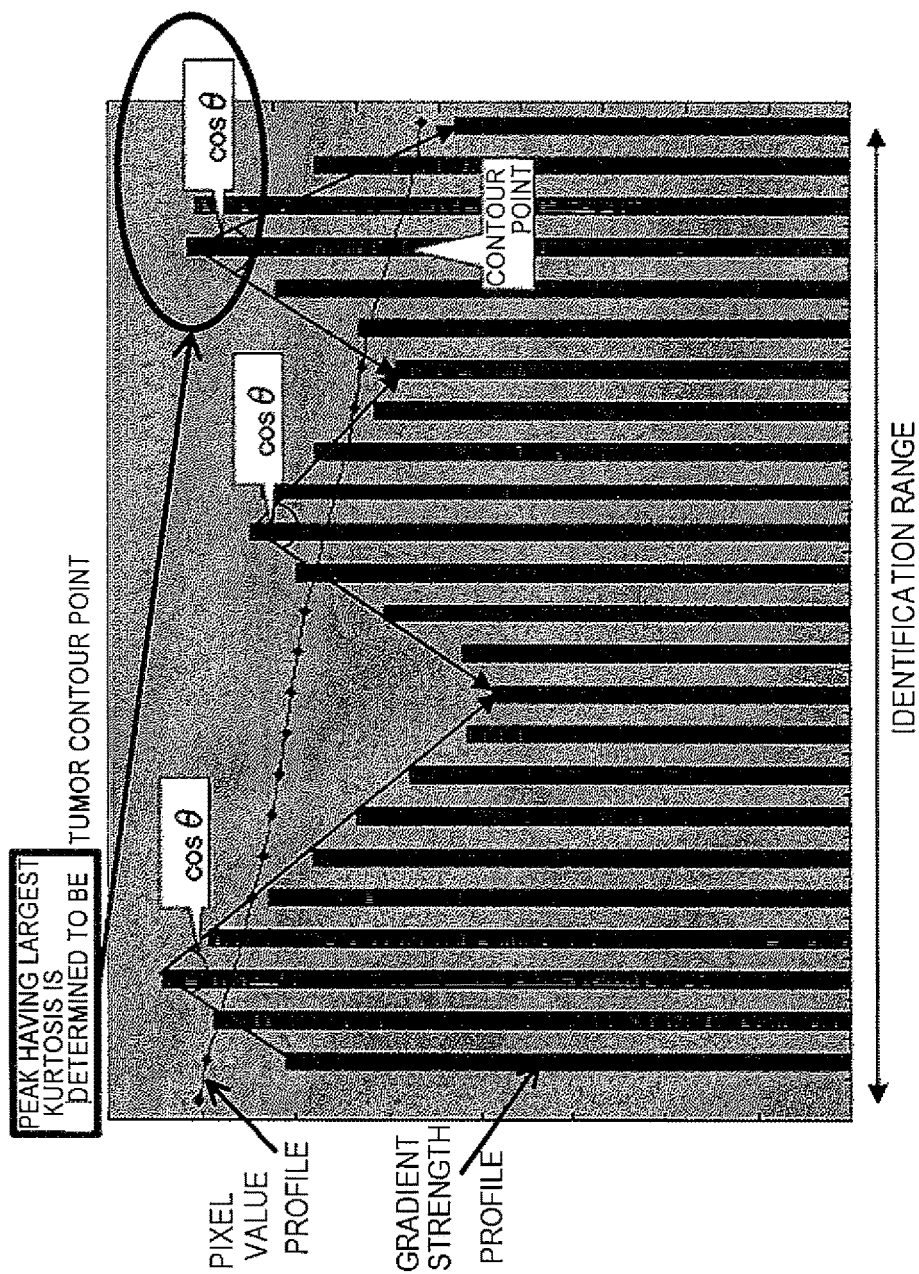
FIG. 10B is a diagram exemplifying a process performed in step 722 for determining a tumor contour point.

FIG. 10A and FIG. 10B each illustrate a process for determining a contour point. FIG. 10A corresponds to the case of substep 2 described above where only one peak is detected in the gradient strength profile within the identification range. Thus, the point on the pixel value profile corresponding to the peak is extracted as a tumor contour point.

In contrast, FIG. 10B corresponds to the case of substep 3 described above where a plurality of peaks are detected in the gradient strength profile within the identification range. In this case, the kurtosis of each peak is calculated, and the peak having the largest kurtosis (that is, the peak having the largest cos θ value) is extracted as a tumor contour point.

Note that the processing from step 714 to 722 is performed on each of all the pixel value profiles created in step 712. For example, as described above, 64800 pixel value profiles in total have been created so as to create the extracted contour exemplified in FIG. 11. Each of all the pixel value profiles is processed individually from step 714 to step 722.

Figure 11:
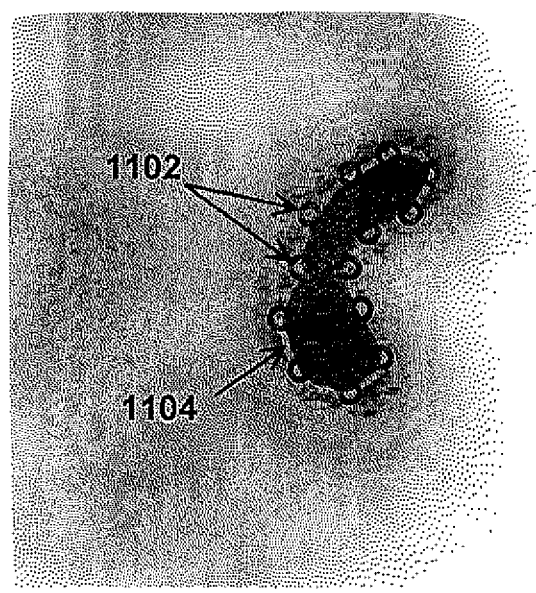
FIG. 11 is a diagram exemplifying a display of extracted contour points performed in step 724.

In step 724, the extracted contour points are displayed. In some embodiments, the extracted contour points may be connected as a closed curve. FIG. 11 exemplifies a display of the extracted contour points. FIG. 11 illustrates contour points 1102 and a contour 1104 extracted for the tumor region 802 illustrated in FIG. 8A and FIG. 8B. One contour point 1102 should basically be determined on each of the pixel value profiles created in step 712 (a contour point may be unobtainable due to an error or other causes). Although FIG. 11 illustrates only 13 contour points 1102 in total, far more contour points 1102 have actually been determined. The closed curve 1104 is created by connecting the extracted contour points 1102.

Step 726 indicates the end of processing.

The step 700 automatically extracts the contour of a tumor. This configuration reduces the variation in the results of extraction performed by different operators, enabling subjective extraction of tumor contours. In the present example, the whole processing, except the selection of a reference point in step 710, is automatically performed to extract a contour, requiring significantly small effort from an operator for extracting the contour.

Preferred embodiments of the technical ideas disclosed in the present description have been described above; however, it is needless to say that the embodiments of the technical ideas are not limited to those described above. The above embodiments are merely examples, and various other embodiments can be present.

Figure 12:
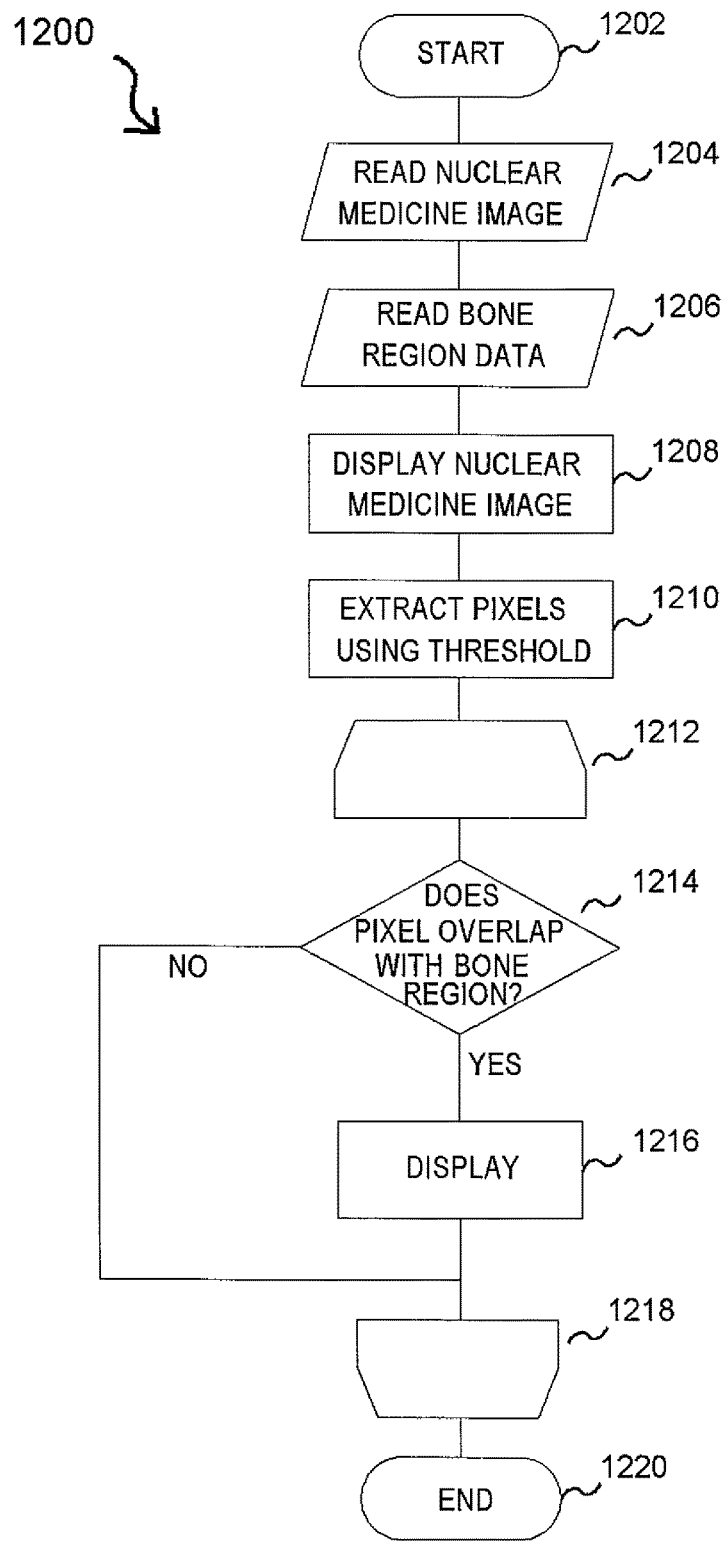
FIG. 12 is a flowchart illustrating an application example 1200 of the process 200 described with reference to the flowchart in FIG. 2.

For example, a usage of the process 200, which has been described with reference to the flowchart in FIG. 2, is exemplified with reference to FIG. 12. A process 1200 illustrated in FIG. 12 relates to a method for analyzing and displaying a nuclear medicine image, and to a method for displaying an accumulation due to a lesion of bone in a manner identifiable by an operator.

Step 1202 indicates the start of processing. In step 1204, the nuclear medicine image data 130 subject to the process 1200 is read. In step 1206, the bone region data 134 stored in step 212 of the process 200 in FIG. 2 is read.

In step 1208, an appropriate section is cut out of the nuclear medicine image data 130 and is displayed as an image. A section to be cut out may be, for example, a section including a pixel having the largest pixel value in the bone region. In step 1210, on the same sectional image, an appropriate threshold is used to distinguish accumulations due to tumors or other causes so as to extract pixels having the pixel values equal to or larger than the threshold.

In the loop indicated from step 1212 to step 1218, each of the extracted pixels is compared with the bone region data read in step 1206, and determined whether it overlaps the bone region (step 1214). If the pixel is determined to be overlapping the bone region, the location corresponding to the pixel is displayed on the image displayed in step 1208, in a manner visually identifiable by an operator. For example, the pixel is displayed in a clearly distinguishable color, such as red. In contrast, if the pixel is determined to be not overlapping the bone region, such display is not performed and the determination is performed on the next pixel.

After the determination processing in step 1214 is completed on all the pixels extracted in step 1210, the process 1200 exits the loop and ends the processing (step 1220).

Figure 13B:
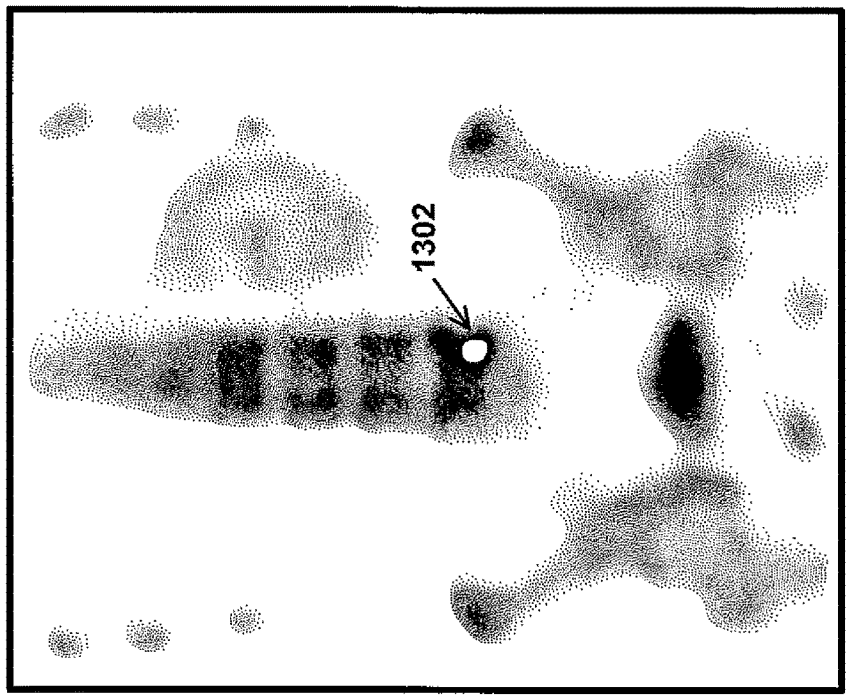
FIG. 13A and FIG. 13B are diagrams exemplifying an effect of the process 1200.
Figure 13A:
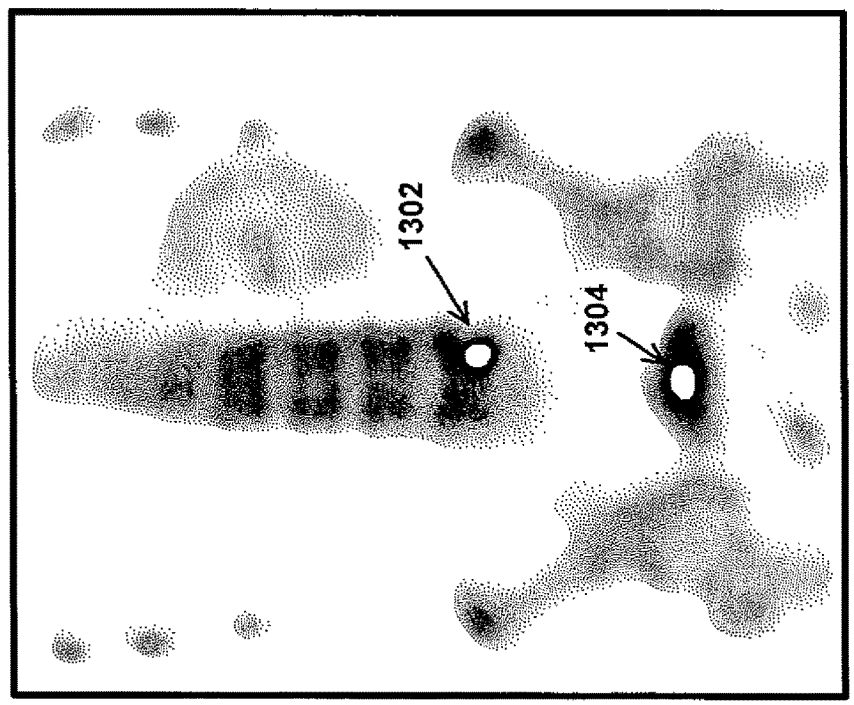

The display provided by the process 1200 is described by taking FIG. 13 as an example. FIG. 13A illustrates a sectional image of the nuclear medicine image data 130 in which pixels having the pixel values equal to or larger than the same threshold used in step 1210 are displayed in white. The locations demoted by symbols 1302 and 1304 indicate that the pixels having the pixel values equal to or larger than the threshold are present. However, the large pixel values in the location denoted by symbol 1304 are caused by physiological accumulation and not by the accumulation due to tumors or other causes. In contrast, FIG. 13B illustrates a display created by the process 1200 that identifiably displays only the region having the pixel values equal to or larger than a certain threshold and overlapping the bone region, and does not identifiably display the region having the pixel values equal to or larger than the certain threshold but not overlapping the bone region. As compared to FIG. 13A, the accumulation 1302 observed in the bone region is highlighted as in FIG. 13A, but the physiological accumulation 1304 is not highlighted. That is, the process 1200 eliminates the effect of physiological accumulation to allow clear observation of only the accumulation due to a lesion of bone.

In FIG. 13, the highlight is made in white; however, it is not appropriate because white is used for depicting other regions as well. In practice, this highlight is preferably made in color. FIG. 13 and other drawings in the present application do not use colors only because of the limitation that the drawings of a patent application are not allowed to use colors.

The technical ideas disclosed in the present description may be presented as various other embodiments.

Individual features included in the various examples that have been described in the description or the drawings are not limited to usage with examples in which these features are explicitly explained to be included, but may be used in combination with other examples that have been described herein or various specific examples that have not been described. In particular, the processes presented in the flowcharts do not necessarily need to be performed in the described order. According to the preference of an executor, the processes may be performed in a changed order or in parallel, or as a plurality of blocks integrally implemented, or in a loop as appropriate. These variations are all included in the scope of the invention disclosed in the present application. The form of implementing processes does not limit the scope of the invention. The order of the description of the processes defined in the claims does not necessarily specify the mandatory order of the processes. For example, an embodiment specifying a different order of the processes and an embodiment that executes the processes in a loop are also included in the scope of the invention according to the claims. It should be noted that the applicant claims to possess the right to have a patent granted on all the embodiments not deviating from the spirit of the invention regardless of whether a patent is claimed in the current set of attached claims.

REFERENCE SIGNS LIST 100 system
102 CPU
104 main memory
106 large-capacity storage unit
107 display interface
108 peripheral device interface
109 network interface
110 operating system
120 nuclear medicine image analysis program
130-138 data

The invention claimed is:

1. A non-transitory computer readable medium having a stored computer program for automatically extracting a tumor contour from three-dimensional nuclear medicine image data, the computer program comprising a first program instruction group that is configured, when executed by at least one processor of a system, to cause the system to execute:
setting a reference point in a region including a tumor on the nuclear medicine image data;
scanning pixels radially and three-dimensionally from the reference point, and creating a pixel value profile in each scanning direction;
creating a gradient strength profile for the pixel value profile or for the pixel value profile to which smoothing has been applied;
setting a range for identifying contour in the pixel value profile or in the pixel value profile to which smoothing has been applied; and
determining a tumor contour point in the pixel value profile within the range for identifying contour, based on a peak having the largest kurtosis in the corresponding gradient strength profile or in the corresponding gradient strength profile to which smoothing has been applied,
wherein the kurtosis is a cosine of an angle between two vectors extending from an extreme point giving a maximal value to respective adjacent extreme points giving minimal values, in the gradient strength profile or in the gradient strength profile to which smoothing has been applied.

2. The non-transitory computer readable medium according to claim 1, wherein the setting of the range for identifying contour is performed based on an extreme point in the pixel value profile or in the pixel value profile to which smoothing has been applied.

3. The non-transitory computer readable medium according to claim 1, wherein the region including a tumor is a region determined to be a region having pixel values equal to or larger than a certain threshold, in the nuclear medicine image data.

4. The non-transitory computer readable medium according to claim 1, further comprising a second program instruction group that is configured to cause, when executed by the at least one processor, the system to execute:
acquiring a pixel group of a region corresponding to a bone from a pixel group included in the nuclear medicine image data;
obtaining a standard deviation based on pixel values of at least a part of the acquired pixel group; and
extracting a bone tumor pixel group based on the standard deviation, the first program instruction group being further configured to cause, when executed by the at least one processor of the system, the system to set the extracted bone tumor pixel group to the region including a tumor.

5. The non-transitory computer readable medium according to claim 4, further configured to cause the system to execute:
creating a histogram based on the pixel values of the acquired pixel group;
determining a peak value in the histogram; and
determining two class values having respective frequencies of a certain percentage of the peak value in the histogram,
the at least a part of the acquired pixel group being a group of pixels having pixel values included in an interval defined by the two class values.

6. The non-transitory computer readable medium according to claim 5, wherein the extracting a bone tumor pixel group based on the standard deviation comprises extracting a bone tumor pixel group based on the standard deviation and a larger one of the two class values.

7. The non-transitory computer readable medium according to claim 4, wherein the extracting a bone tumor pixel group based on the standard deviation comprises extracting a bone tumor pixel group based on the standard deviation and an average value calculated based on the pixel values of the at least a part of the acquired pixel group.

8. The non-transitory computer readable medium according to claim 7, wherein the acquiring a pixel group of a region corresponding to a bone comprises:
extracting a bone region from CT image data that has been aligned with the nuclear medicine image data; and
extracting, from the nuclear medicine image data, a pixel group of a region overlapping the extracted bone region.

9. A method for analyzing nuclear medicine image data, the method being executed by a system when a program instruction is executed by at least one processor of the system, the method comprising:
setting a reference point in a region including a tumor on the nuclear medicine image data;
scanning pixels radially and three-dimensionally from the reference point, and creating a pixel value profile in each scanning direction;
creating a gradient strength profile for the pixel value profile or for the pixel value profile to which smoothing has been applied;
setting a range for identifying contour in the pixel value profile or in the pixel value profile to which smoothing has been applied; and
determining a tumor contour point in the pixel value profile within the range for identifying contour, based on a peak having the largest kurtosis in the corresponding gradient strength profile or in the corresponding gradient strength profile to which smoothing has been applied,
wherein the kurtosis is a cosine of an angle between two vectors extending from an extreme point giving a maximal value to respective adjacent extreme points giving minimal values, in the gradient strength profile or in the gradient strength profile to which smoothing has been applied.

10. An apparatus comprising:
at least one processor; and
at least one non-transitory memory including computer program code, the at least one memory and the computer program code configured to, with the at least one processor, cause the apparatus to:
  set a reference point in a region including a tumor on the nuclear medicine image data;
  scan pixels radially and three-dimensionally from the reference point, and creating a pixel value profile in each scanning direction;
  create a gradient strength profile for the pixel value profile or for the pixel value profile to which smoothing has been applied;
  set a range for identifying contour in the pixel value profile or in the pixel value profile to which smoothing has been applied; and
  determine a tumor contour point in the pixel value profile within the range for identifying contour, based on a peak having the largest kurtosis in the corresponding gradient strength profile or in the corresponding gradient strength profile to which smoothing has been applied,
  where the kurtosis is a cosine of an angle between two vectors extending from an extreme point giving a maximal value to respective adjacent extreme points giving minimal values, in the gradient strength profile or in the gradient strength profile to which smoothing has been applied.

11. The apparatus according to claim 10 where the setting of the range for identifying contour is configured to be performed based on an extreme point in the pixel value profile or in the pixel value profile to which smoothing has been applied.

12. The apparatus according to claim 10 where the region including a tumor is a region determined to be a region having pixel values equal to or larger than a certain threshold, in the nuclear medicine image data.

13. The apparatus according to claim 10 further comprising a second program instruction group that is configured, when executed by the at least one processor, to cause the system to execute:

acquiring a pixel group of a region corresponding to a bone from a pixel group included in the nuclear medicine image data;
  obtaining a standard deviation based on pixel values of at least a part of the acquired pixel group; and
  extracting a bone tumor pixel group based on the standard deviation,
  the first program instruction group being further configured to cause, when executed by the at least one processor of the system, the system to set the extracted bone tumor pixel group to the region including a tumor.

14. The apparatus according to claim 13 further configured to cause the system to execute:
  creating a histogram based on the pixel values of the acquired pixel group;
  determining a peak value in the histogram; and
  determining two class values having respective frequencies of a certain percentage of the peak value in the histogram,
  the at least a part of the acquired pixel group being a group of pixels having pixel values included in an interval defined by the two class values.

15. The apparatus according to claim 14 where the extracting a bone tumor pixel group based on the standard deviation comprises extracting a bone tumor pixel group based on the standard deviation and a larger one of the two class values.

16. The apparatus according to claim 13, wherein the extracting a bone tumor pixel group based on the standard deviation comprises extracting a bone tumor pixel group based on the standard deviation and an average value calculated based on the pixel values of the at least a part of the acquired pixel group.

17. The apparatus according to claim 16 where the acquiring a pixel group of a region corresponding to a bone comprises:
  extracting a bone region from CT image data that has been aligned with the nuclear medicine image data; and
  extracting, from the nuclear medicine image data, a pixel group of a region overlapping the extracted bone region.

* * * * *